United States Patent [19]

Gerbal et al.

[11] Patent Number: 4,605,697

[45] Date of Patent: Aug. 12, 1986

[54] SUBSTITUTED SULFONAMIDO COMPOUNDS, PHOTOSENSITIVE ELEMENTS, FILM UNITS, AND PROCESSES FOR RETAINING A PHOTOGRAPHIC IMAGE WITH SAME

[75] Inventors: Claude F. Gerbal, Bonneuil-sur-Marne, France; Thomas E. Gompf, Rochester, N.Y.; Pierre D. Collet, Nogent-sur-Marne, France

[73] Assignee: Eastman Kodak Company, Rochester, N.Y.

[21] Appl. No.: 533,075

[22] Filed: Sep. 16, 1983

Related U.S. Application Data

[60] Continuation of Ser. No. 150,037, May 15, 1980, abandoned, which is a division of Ser. No. 3,972, Apr. 24, 1979, Pat. No. 4,258,120.

[51] Int. Cl.$^4$ .................. C09B 43/00; C09B 43/12; C09B 43/124; C09B 43/132
[52] U.S. Cl. ............................ 534/648; 534/573; 534/592; 534/649; 534/651; 534/734
[58] Field of Search .............. 260/162, 152, 155, 154, 260/157, 158, 198, 199, 200; 534/648, 649, 651

[56] References Cited

U.S. PATENT DOCUMENTS

| | | | |
|---|---|---|---|
| 3,728,113 | 4/1973 | Becker et al. | 96/3 |
| 3,751,406 | 8/1973 | Bloom | 260/162 |
| 3,928,312 | 12/1975 | Fleckenstein | 260/156 |
| 4,110,355 | 8/1978 | Bloom | 260/372 |

FOREIGN PATENT DOCUMENTS 2154443 6/1973 France ........................ 96/3

Primary Examiner—Floyd D. Higel
Attorney, Agent, or Firm—William J. Davis

[57] ABSTRACT

A nondiffusible sulfonamido compound which is alkali-cleavable upon oxidation to release a diffusible photographically useful material, said nondiffusible sulfonamido compound having the formula:

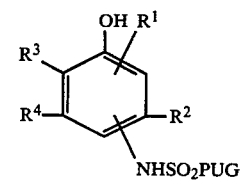

wherein:
(a) $R^1$ is alkyl, aryl sulfamyl, carbamyl, carbonamido, carbonyl, carbonyloxy or sulfonamido;
(b) $R^2$ is alkyl having from 1 to 18 carbon atoms, aryl, or alkylphenyl having from 7 to 12 carbon atoms;
(c) $R^3$ and $R^4$ are independently alkyl, or aryl, or $R^3$ and $R^4$, taken together, form a fused carbocyclic or heterocyclic ring;
(d) NHSO$_2$PUG represents a sulfonamido group;
(e) PUG represents a photographically useful group; and
(f) at least one of $R^1$, $R^2$, $R^3$, or $R^4$, or any combination thereof, provides a molecular configuration of such size or shape as to render the compound nondiffusible under alkaline processing conditions,
is useful as redox releaser in photosensitive elements, photographic film units and in processes for transferring and/or retaining a photographic image in color diffusion transfer units. These elements, film units and processes produce retained color images having substantially reduced minimum densities.

5 Claims, No Drawings

SUBSTITUTED SULFONAMIDO COMPOUNDS, PHOTOSENSITIVE ELEMENTS, FILM UNITS, AND PROCESSES FOR RETAINING A PHOTOGRAPHIC IMAGE WITH SAME

This is a continuation, of application Ser. No. 150,037, filed May 15, 1980, now abandoned, which application is a division of application Ser. No. 032,972, filed Apr. 24, 1979, issued on Mar. 24, 1981, as U.S. Pat. No. 4,258,120.

BACKGROUND OF THE INVENTION

1. Field of the Invention

This invention relates to photography and more particularly to color diffusion transfer photography employing sulfonamido compounds which are preferably alkali-cleavable upon oxidation to release a diffusible photographically useful group.

2. Description Relative to the Prior Art

Various formats for color diffusion transfer assemblages are described in the prior art, such as U.S. Pat. Nos. 2,543,181; 2,983,606; 3,362,819; 3,362,821; 3,592,645; 3,785,815; 3,415,644; 3,415,645; 3,415,646; 3,647,437; 3,685,707 and 3,756,815, and Canadian Pat. Nos. 928,559 and 674,082. In these formats, the image-receiving layer containing the photographic image for viewing can be separated from the photographic layers after processing, or, in some embodiments, it can remain permanently attached and integral with the image-generating and ancillary layers present in the structure when a transparent support is employed on the viewing side of the assemblage. The image is formed by color-providing substances released from the image-generating units, diffusing through the layers of the structure to the dye image-receiving layer. After exposure of the assemblage, an alkaline processing composition permeates the various layers to initiate development of the exposed photosensitive silver halide emulsion layers. The emulsion layers are developed in proportion to the extent of the respective exposures, and the image dyes which are formed or released in the respective image-generating layers begin to diffuse throughout the structure. At least a portion of the imagewise distribution of color-providing substances can diffuse to a dye image-receiving layer to form an image of the original subject in that layer. A retained image is also obtained consisting of the dye-providing compound that remains in the unexposed areas.

A process of this type is described in French Pat. No. 2,154,443 wherein a photographic film unit is used which comprises at least one dye image-providing element consisting of at least one silver halide light-sensitive element having associated therewith a nondiffusible compound capable of releasing a dye, hereinafter referred to as a redox releaser. The redox releaser comprises a sulfonamidophenol or sulfonamidoaniline moiety and a dye or dye precursor moiety which can be released during photographic processing by an oxidation-reduction reaction. After imagewise exposure, the photographic film unit is processed with an alkaline solution in the presence of a silver halide developing agent. In each dye image-providing element, a negative silver image is developed and an imagewise distribution of oxidized developing agent is formed which is cross-oxidized with the nondiffusible dye image-providing redox releaser. As a result, an alkali-cleavable compound is formed which will release a diffusible dye or dye precursor as a function of the exposure received by each of the silver halide light-sensitive layers. The diffusible dye images formed in each image-providing element are then removed, either by allowing them to migrate by diffusion into the processing bath, or by transferring them onto a mordant-containing sheet. A retained image is also obtained in the photographic film unit. If the silver halide light-sensitive emulsions of the film unit are negative emulsions, i.e., emulsions that give negative images upon exposure to a positive original, the retained image is a redox releaser color image positive with respect to the the original. In this case, the redox releaser is a color compound or a compound which becomes colored upon processing. The photographic film unit which carries the positive color image comprises also a negative silver image and a positive imagewise distribution of unexposed and undeveloped silver halides. If it is desirable to keep the positive color image only, it is necessary to remove by known processes the residual silver halides and the developed silver image, for example by bleaching followed by fixing, such as described in U.S. Pat. No. 3,923,510.

In many instances, the dye images obtained as described above do not exhibit satisfactory sensitometric characteristics. In particular, minimum densities are often undesirably high. In the prior art processes in which the retained image is kept, the image must be bleached to obtain a satisfactory minimum density.

These prior art processes, such as described in the aforementioned French Pat. No. 2,154,443 have, in particular, the disadvantage of providing minimum densities which contribute to the formation of unwanted stain. Without the following theory limiting the scope of the present invention, it may be assumed that the stain results from the following reaction mechanisms:

1. As previously mentioned, the redox releaser is oxidized upon processing and releases a diffusible dye (or dye precursor) but it also releases a nondiffusible quinone, this reaction being represented as follows:

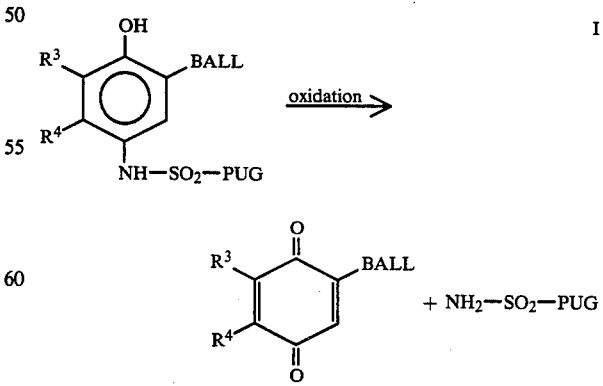

2. The quinone formed is subjected to a hydroxylation reaction, generally in the 3-position, represented by the following mechanism:

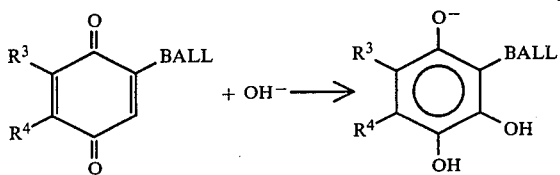

3. This hydroxylation product is then oxidized into a hydroxyquinone, which reaction is represented as follows:

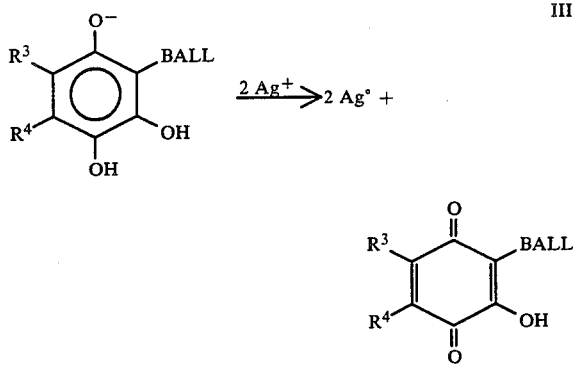

This 3-hydroxyquinone which is insoluble in the processing solution and remains in the processed photographic film unit is yellow in color and contributes substantially to the stain in the retained color images. The use of redox releasers which are substituted, for example, in the 3-position, would prevent the formation of the 3-hydroxyquinones responsible for unwanted stain according to the above reaction mechanisms. It is thus seen that substituted sulfonamido compounds are desirable for use as redox releasers in photosensitive elements, film units, and processes for retaining a color photographic image with reduced stain.

SUMMARY OF THE INVENTION

The compounds of the invention are nondiffusible sulfonamido compounds which are alkali-cleavable upon oxidation to release a diffusible photographically useful material and can be represented by the following formula:

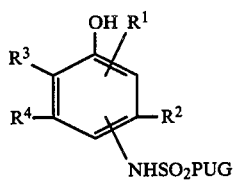

wherein:
  (a) $R^1$ is alkyl, aryl, sulfamyl, carbamyl, carbonamido, carbonyl, carbonyloxy or sulfonamdio;
  (b) $R^2$ is alkyl having from 1 to 18 carbon atoms, aryl, or alkylphenyl having from 7 to 12 carbon atoms;
  (c) $R^3$ and $R^4$ are independently alkyl, or aryl, or $R^3$ and $R^4$, taken together, form a fused substituted or unsubstituted carbocyclic or heterocyclic ring;
  (d) $NHSO_2PUG$ represents a sulfonamido group;
  (e) PUG represents a photographically useful group; and
  (f) at least one of $R^1$, $R^2$, $R^3$, or $R^4$, or any combination thereof, provides a molecular configuration of such size or shape as to render the compound nondiffusible under alkaline processing conditions.

A photosensitive element according to this invention can comprise a support having thereon at least one photosensitive silver halide emulsion layer having associated therewith at least one redox releaser, wherein each said redox releaser is a nondiffusible sulfonamido compound which is alkali-cleavable upon oxidation to release a diffusible photographically useful material, said non-diffusible sulfonamido compound having the formula:

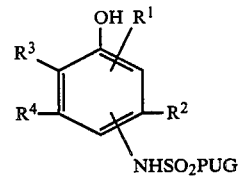

wherein:
  (a) $R^1$ is alkyl, aryl, sulfamyl, carbamyl, carbonamido, carbonyl, carbonyloxy or sulfonamido;
  (b) $R^2$ is alkyl having from 1 to 18 carbon atoms, aryl, or alkylphenyl having from 7 to 12 carbon atoms;
  (c) $R^3$ and $R^4$ are independently alkyl, or aryl, or $R^3$ and $R^4$, taken together, form a fused substituted or unsubstituted carbocyclic or heterocyclic ring;
  (d) $NHSO_2PUG$ represents a sulfonamido group;
  (e) PUG represents a photographically useful group; and
  (f) at least one of $R^1$, $R^2$, $R^3$, or $R^4$, or any combination thereof, provides a molecular configuration of such size or shape as to render the compound nondiffusible under alkaline processing conditions.

This invention also contemplates a photographic film unit containing a silver halide developing agent comprising a support having thereon at least one photosensitive silver halide emulsion layer having associated therewith at least one sulfonamido redox releaser, a dye image-receiving layer and an alkaline processing composition, the improvement wherein said sulfonamido redox releaser has the formula:

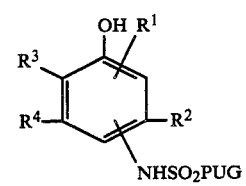

wherein:
  (a) $R^1$ is alkyl, aryl, sulfamyl, carbamyl, carbonamido, carbonyl, carbonyloxy or sulfonamido;
  (b) $R^2$ is alkyl having from 1 to 18 carbon atoms, aryl, or alkylphenyl having from 7 to 12 carbon atoms;
  (c) $R^3$ and $R^4$ are independently alkyl, or aryl, or $R^3$ and $R^4$, taken together, form a fused substituted or unsubstituted carbocyclic or heterocyclic ring;
  (d) $NHSO_2PUG$ represents a sulfonamido group;
  (e) PUG represents a photographically useful group; and
  (f) at least one of $R^1$, $R^2$, $R^3$, or $R^4$, or any combination thereof, provides a molecular configuration of such size or shape as to render the compound nondiffusible under alkaline processing conditions.

Another embodiment of this invention comprises a process of forming an image in a color diffusion transfer unit which comprises contacting an imagewise-exposed photosensitive element comprising a support having coated thereon at least one photosensitive silver halide emulsion layer having associated therewith at least one redox releaser, wherein each said redox releaser is a nondiffusible sulfonamido compound which is alkali-cleavable upon oxidation to release a photographically useful group and an image-receiving layer, said process comprising contacting said photosensitive element with an alkaline processing composition in the presence of a silver halide developing agent, whereby at least a portion of said redox releaser is imagewise transferred by diffusion to the dye receiving layer, the improvement wherein said sulfonamido redox releaser has the formula:

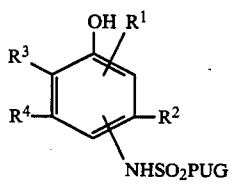

wherein:
(a) $R^1$ is alkyl, aryl, sulfamyl, carbamyl, carbonamido, carbonyl, carbonyloxy or sulfonamido;
(b) $R^2$ is alkyl having from 1 to 18 carbon atoms, aryl, or alkylphenyl having from 7 to 12 carbon atoms;
(c) $R^3$ and $R^4$ are independently alkyl, or aryl, or $R^3$ and $R^4$, taken together, form a fused substituted or unsubstituted carbocyclic or heterocyclic ring;
(d) $NHSO_2PUG$ represents a sulfonamido group;
(e) PUG represents a photographically useful group; and
(f) at least one of $R^1$, $R^2$, $R^3$, or $R^4$, or any combination thereof, provides a molecular configuration of such size or shape as to render the compound nondiffusible under alkaline processing conditions.

In a further embodiment of the invention a process for retaining a photographic image in a color diffusion transfer unit is provided, said process comprising:
(i) imagewise exposing a photosensitive element comprising a transparent support having thereon at least one photosensitive silver halide emulsion layer having associated therewith at least one redox releaser, wherein each said redox releaser is a nondiffusible sulfonamido compound which is alkali-cleavable upon oxidation to release a photographically useful group, and
(ii) contacting said photosensitive element with an alkaline processing composition in the presence of a silver halide developing agent, whereby at least a portion of said redox releaser is imagewise eliminated by diffusion in a solution or by mordanting on a strippable support, thus forming in the retained product an image corresponding to the photographically useful group remaining in the unit, the improvement wherein said sulfonamido redox releaser has the formula:

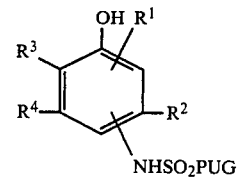

wherein:
(a) $R^1$ is alkyl, aryl, sulfamyl, carbamyl, carbonamido, carbonyl, carbonyloxy or sulfonamido;
(b) $R^2$ is alkyl having from 1 to 18 carbon atoms, aryl, or alkylphenyl having from 7 to 12 carbon atoms;
(c) $R^3$ and $R^4$ are independently alkyl, or aryl, or $R^3$ and $R^4$, taken together, form a fused substituted or unsubstituted carbocyclic ring or heterocyclic ring;
(d) $NHSO_2PUG$ represents a sulfonamido group;
(e) PUG represents a photographically useful group; and
(f) at least one of $R^1$, $R^2$, $R^3$, or $R^4$, or any combination thereof, provides a molecular configuration of such size or shape as to render the compound nondiffusible under alkaline processing conditions.

DETAILED DESCRIPTION OF THE PREFERRED EMBODIMENTS

The novel nondiffusible sulfonamido compound, which is alkali-cleavable upon oxidation to release a diffusible photographically useful material, is represented by the formula:

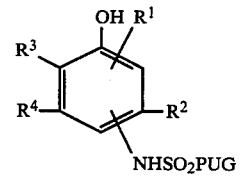

wherein:
$R^1$ is substituted or unsubstituted alkyl, preferably having from 1 to 22 carbon atoms, such as methyl, ethyl, hydroxyethyl, propyl, butyl, secondary butyl, tert-butyl, cyclopropyl, 4-chlorobutyl, cyclobutyl, 4-nitroamyl, hexyl, cyclohexyl, octyl, decyl, octadecyl, docosyl, benzyl, phenethyl, tolyl butyl, isopropyl, sec-dodecyl, t-butyl phenylethyl and the like; aryl, preferably having from 6 to 10 carbon atoms, including phenyl, naphthyl and aryl groups substituted such as described for the above alkyl group, lined directly or indirectly to the above nucleus; sulfamyl; carbamyl; carbonamido preferably having from 8 to 30 carbon atoms; carbonyl preferably having from 8 to 30 carbon atoms; carboxyloxy preferably having from 8 to 30 carbon atoms; sulfonamido, preferably having from 8 to 30 carbon atoms; or ureido, preferably having from 8 to 30 carbon atoms.

$R^2$ is alkyl preferably having from 1 to 18 carbon atoms, such as methyl, ethyl, propyl, isopropyl, tert-butyl, 4-chlorobutyl, hexyl, octyl and the like; aryl, preferably having from 6 to 30 carbon atoms such as phenyl, naphthyl, octylphenyl, dodecyloxyphenyl, dodecylthiophenyl, dodecylsulfamylphenyl and the like; or phenylalkyl preferably having from 7 to 12 carbon atoms, such as benzyl, phenylethyl, phenylpropyl, phenylbutyl, tolyl butyl and the like.

$R^3$ and $R^4$ are independently alkyl, or aryl as described above for $R^1$. Alternatively, $R^3$ and $R^4$, taken together, can form a fused 5 to 8-membered carbocyclic or heterocyclic ring, which may be saturated, such as cyclohexane, pyrrolidine, morpholine, piperidine, tetrahydrofurane, dioxane, quinuclidine, dodecylthiocyclohexane, alkylcyclohexane, phenylcyclohexane, dodecylsulfonylcyclohexane or unsaturated such as benzene, naphthalene, pyrrole, isoxazole, imidazole, isothrazole, furazan; pyrazoline, cyclohexene and the like, and which can further contain additional substituents such as alkyl, alkylthio, alkylsulfonamido and others as described for $R^1$ above;

NHSO$_2$PUG represents a sulfonamido group;

PUG represents a photographically useful group, such as a dye, dye precursor, development inhibitor, development accelerator, bleach inhibitor, bleach accelerator, antifoggant, complexing agent, reducing agent, competer, and the like; and at least one of $R^1$, $R^2$, $R^3$ or $R^4$, or any combination thereof, provides a molecular configuration of such size or shape as to render the compound nondiffusible under alkaline processing conditions.

According to various preferred embodiments of the above-described formula, $R^1$ can represent an organic ballast group, providing a molecular configuration of such size or shape so as to render the compound nondiffusible under alkaline processing conditions, $R^2$ can be alkyl having from 1 to 6 carbon atoms or phenyl, $R^3$ and $R^4$ can be alkyl or, taken together with the above-described formula, form a naphthol nucleus, and PUG can represent a dye or dye precursor.

As indicated by the above formula, the positiions of $R^1$ and —NHSO$_2$PUG can be varied. $R^2$ must occupy the 3-position of the above-described phenol nucleus, and $R^1$ and NHSO$_2$PUG can freely occupy the 2- or 4-position of the above-described phenol nucleus. Preferably $R^1$ occupies the 2-position, $R^2$ occupies the 3-position and NHSO$_2$PUG occupies the 4-position of the above-described phenol nucleus.

When $R^1$ represents an organic ballast group, the nature of the ballast group is not critical as long as long as it confers nondiffusibility to the compounds. Typical ballast groups include long-chain alkyl groups linked directly or indirectly to the above-described phenol nucleus, as well as aromatic radicals of the benzene and naphthalene series indirectly attached or fused directly to the phenol nucleus. Useful ballast groups generally have at least eight carbon atoms such as a substituted or unsubstituted alkyl group of 8 to 22 carbon atoms, a carbamoyl radical having 8 to 30 carbon atoms, a carbonyl radical having 8 to 30 carbon atoms or a sulfamoyl radical having 9 to 30 carbon atoms. Particularly preferred are those that are linked to the above-described phenol nucleus by a —CONH— or —SO$_2$NH— group.

Examples of particularly useful ballast groups include the following groups:

—C$_{15}$H$_{31}$   —C$_{18}$H$_{37}$   —CON(C$_{12}$H$_{25}$)$_2$   —CONHC$_{18}$H$_{37}$

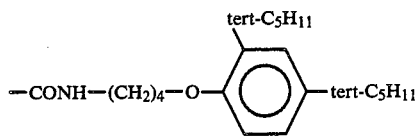

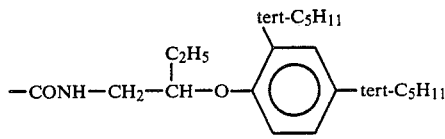

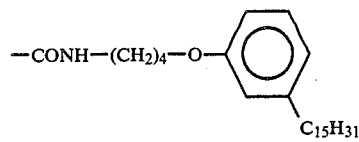

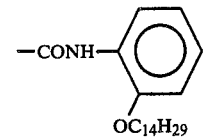

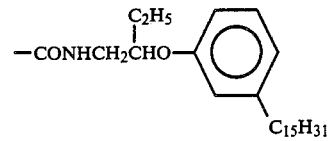

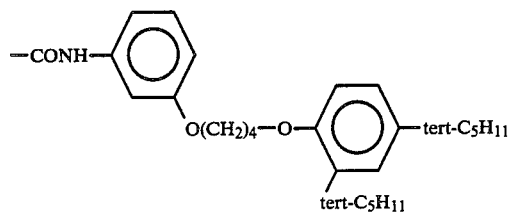

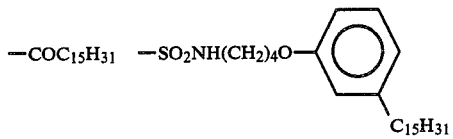

As indicated above, PUG can represent a dye or a dye precursor. These compounds are well known in the art and include dyes such as azo, azomethine, azopyrazolone, indoaniline, indophenol, anthraquinone, triarylmethane, alizarin, merocyanine, nitro, quinoline, cyanine, indigoide, phthalocyanine dyes, metal complexed or complexable dyes, and the like. PUG can also represent dye precursors, such as leuco dyes, dyes whose absorption maximum is shifted by hypsochromic or bathochromic effect when subjected to conditions such as a pH modification or a reaction with a material so as to form a complex. PUG can also represent coupler moieties, such as phenols, naphthols, indazalones, open-chain benzoylacetanilides, pivalylacetanilides, malonamides, cyanacetyls, coumerones, pyrazolones, compounds described in U.S. Pat. No. 2,756,142 and the like. These compounds can contain a solubililizing group if desired. Examples of such dye groups are described in U.S. Pat. No. 4,076,529, issued Feb. 28, 1978.

Examples of 3-substituted sulfonamido compounds corresponding to the above formula and useful as redox releasers in photosensitive elements, film units and processes of this invention include the following compounds:

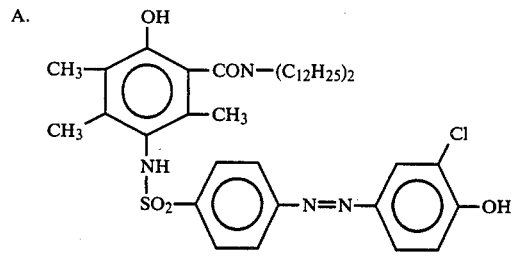
A.
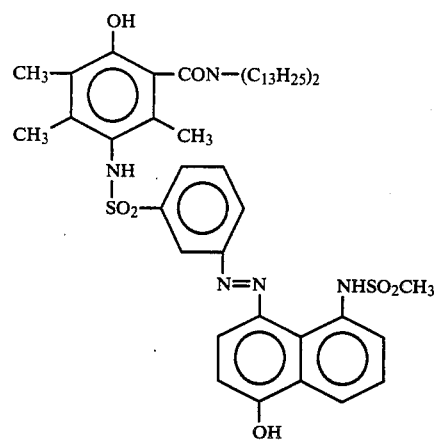
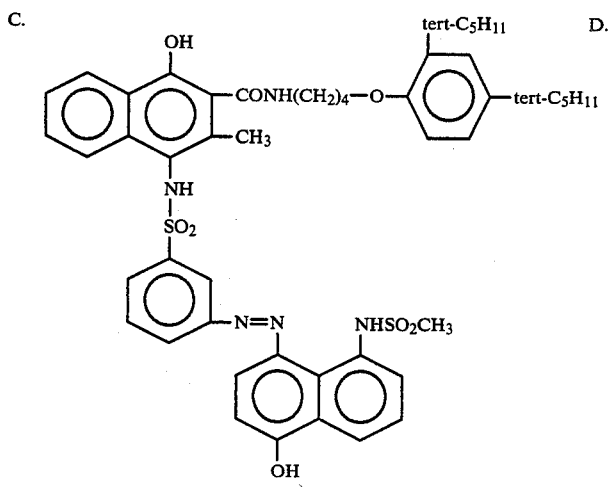
C.
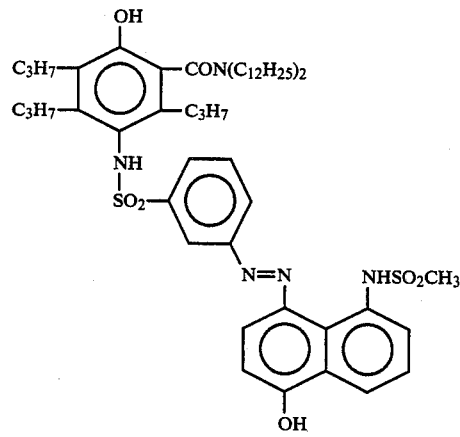
B.
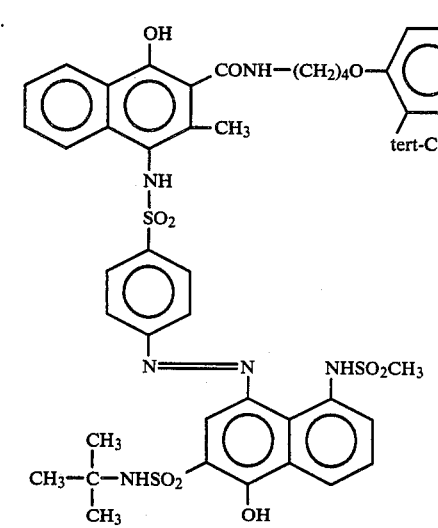
D.
E.
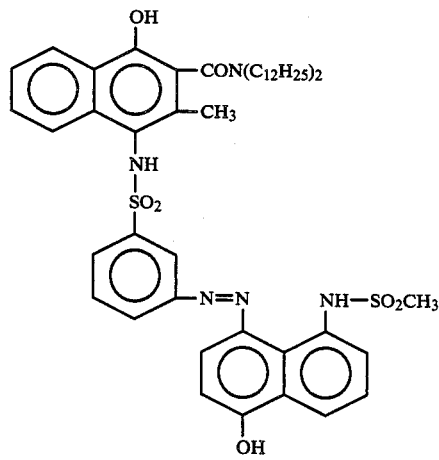
F.

-continued
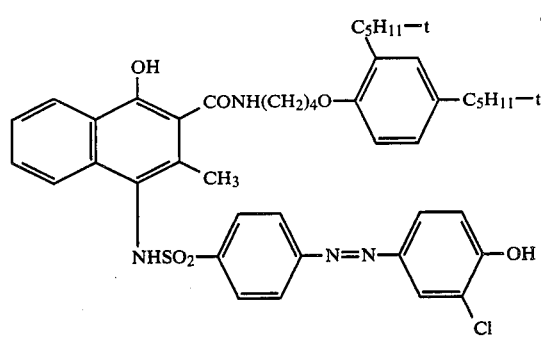
G.
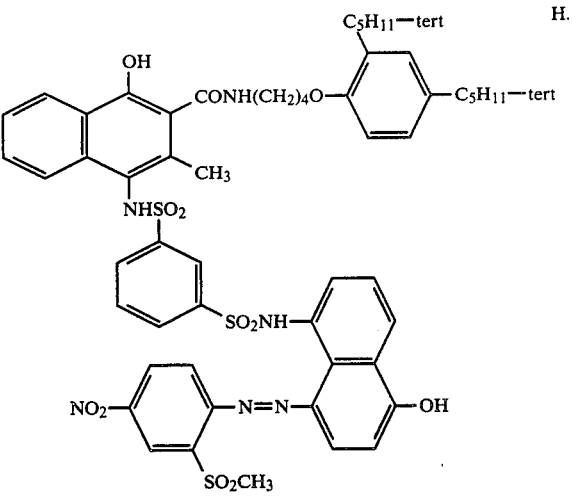
H.
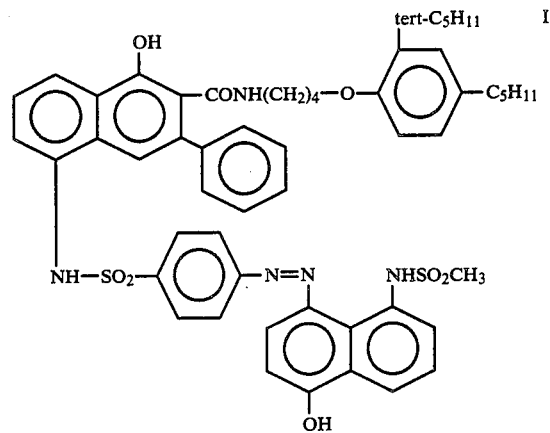
I.
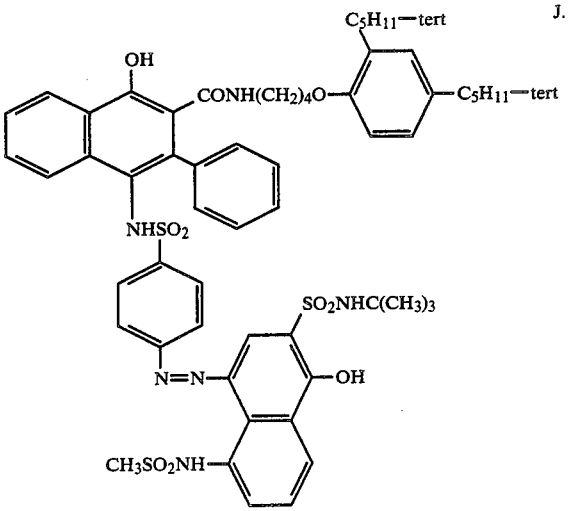
J.
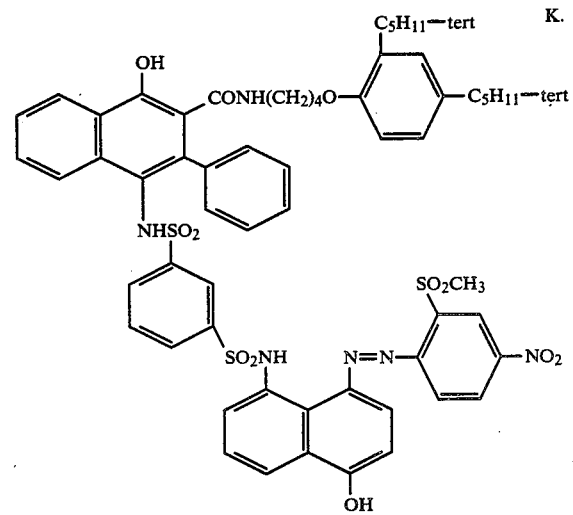
K.
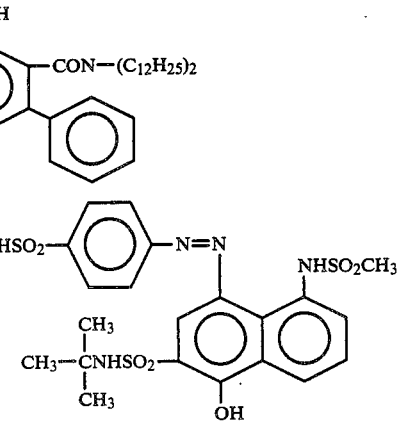
L.

M.

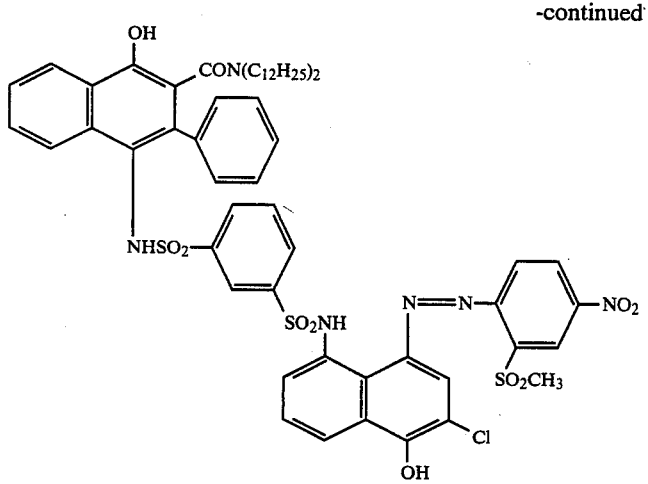

N.

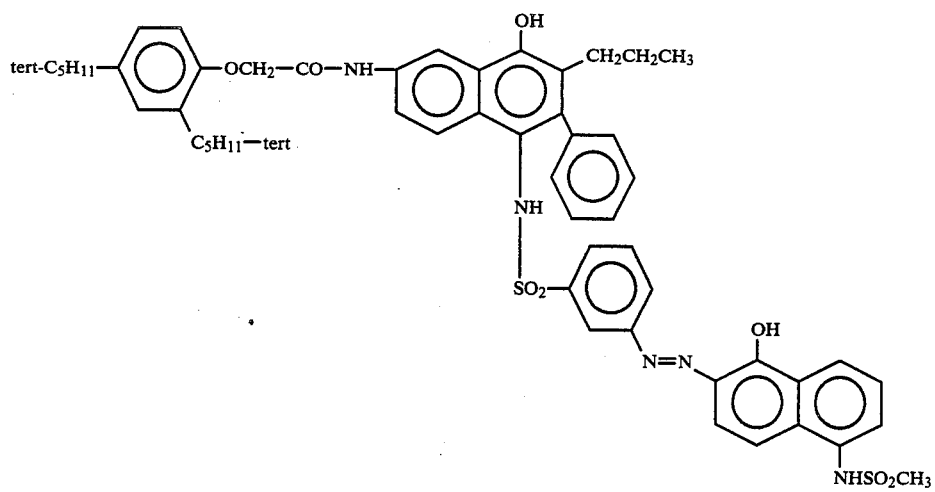

O.

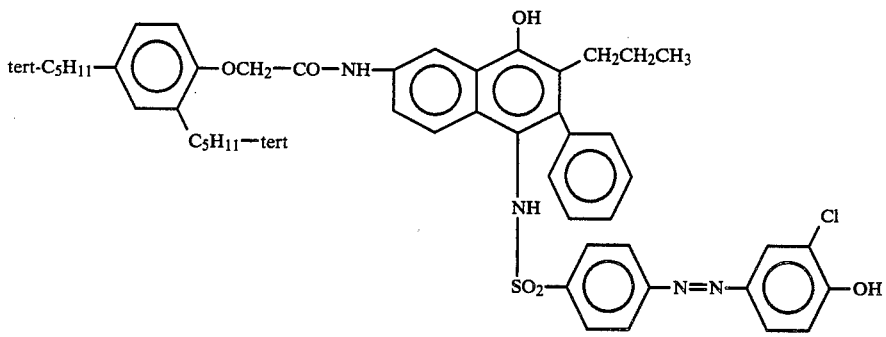

The compounds of the invention can be prepared from readily available chemicals. Various steps of the syntheses of these compounds are relatively simple chemical reactions and can be achieved with satisfactory yields. When the redox releaser corresponds to the following general formula:

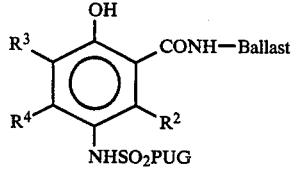

wherein $R^3$ and $R^4$ are alkyl groups, these compounds can be prepared according to the following reactions:

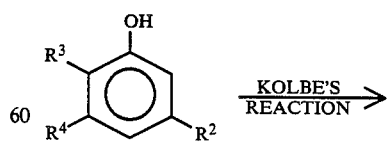

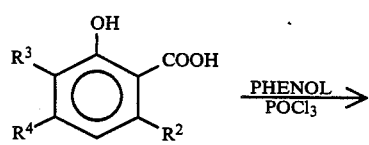

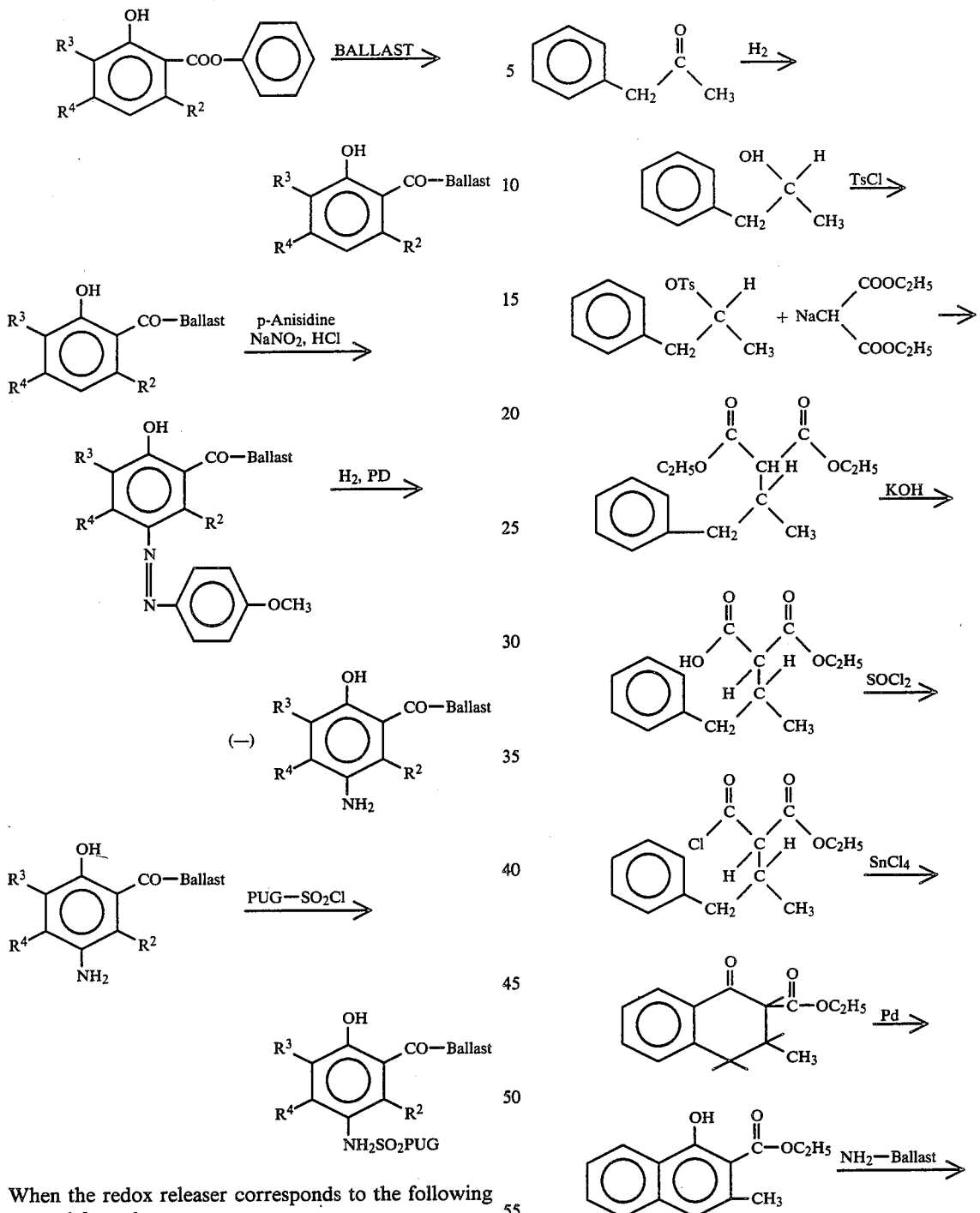
When the redox releaser corresponds to the following general formula:
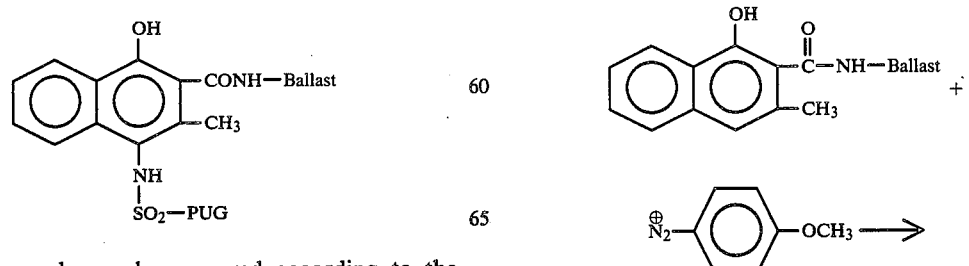
these compounds can be prepared according to the following reactions:

-continued
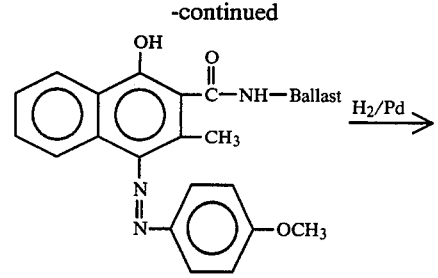
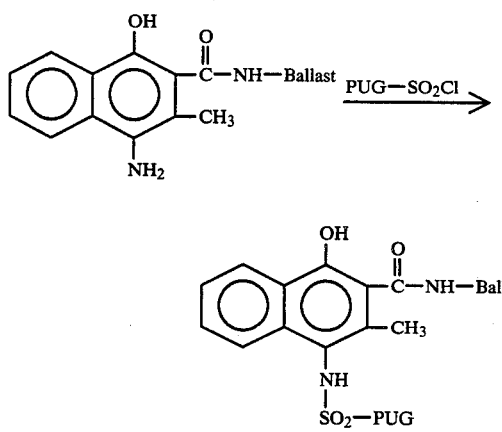
When the redox releaser corresponds to the following general formula:
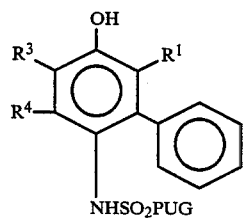
these compounds can be prepared according to the following reaction:
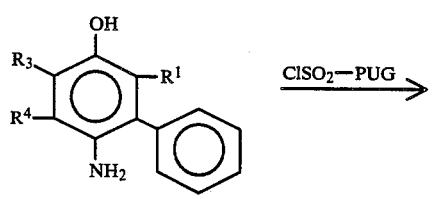
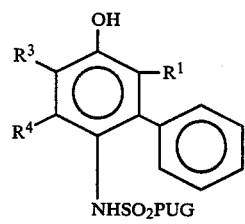
When the redox releaser corresponds to the folowing general formula:
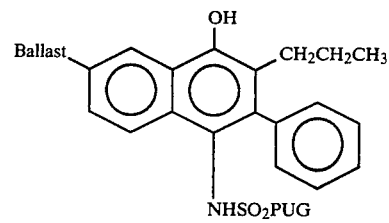
the compounds can be prepared according to the following reactions:
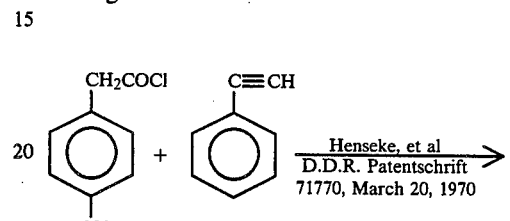
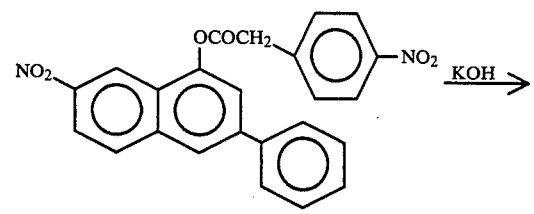
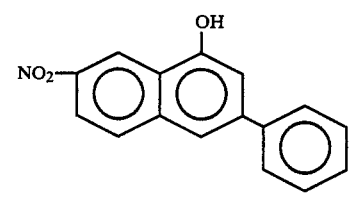
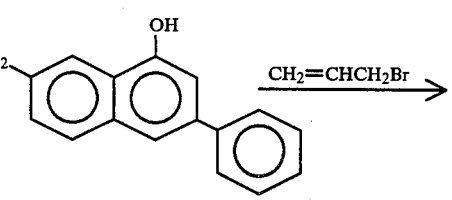
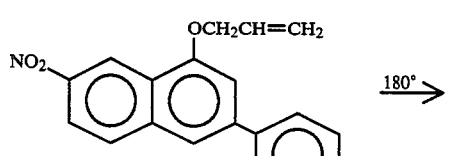
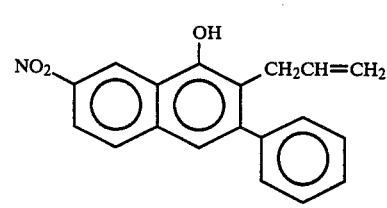

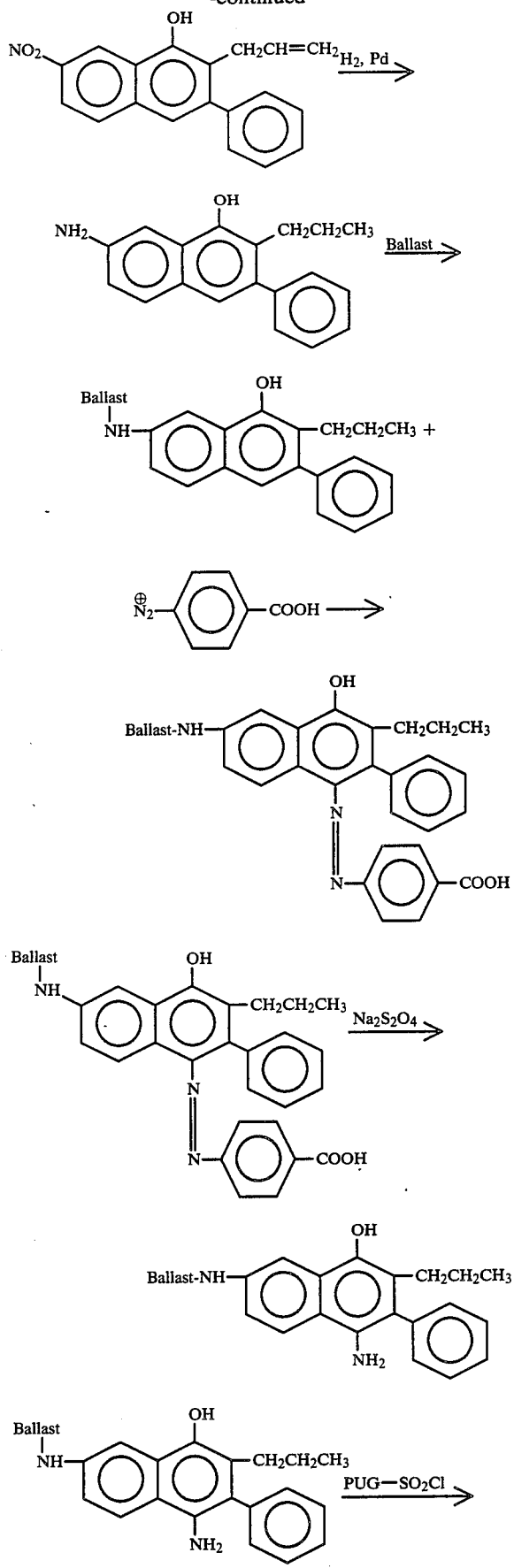
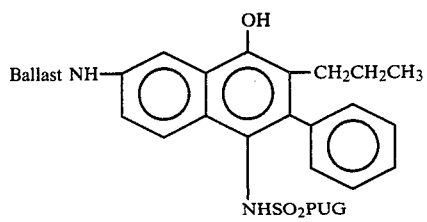

The final step of the above-described reaction sequences can be accomplished by mixing the amine synthesized in the previous steps with PUG-SO$_2$Cl under nitrogen in a suitable solvent, such as anhydrous tetrahydrofuran, methylene chloride, anhydrous pyridine, dimethylformamide, dimethylacetamide, ether, benzene or the like. The ratio of the amine to PUG-SO$_2$Cl can be from about 1:1 to about 1:2; typically the ratio of the amine to PUG-SO$_2$Cl varies from about 1:1 to about 1:1.3. The total volume of solvent used per gram of amine starting material can vary from about 5 to about 30 ml/g. Typically 3 to 8 ml of solvent are employed for every gram of amine starting material. The two reactants can be combined in the selected solvent or they may be combined as two separate solutions, or by adding the PUG-SO$_2$Cl solution dropwise to the amine solution. The reaction mixture can be stirred for 1 to 3 hours under nitrogen at a temperature ranging from 0° to 30° C., or the reaction mixture can be allowed to stand for about 24 hours at about 0° to 30° C.

If the solvent selected does not act as an acid acceptor, an acid acceptor such as pyridine can be added undiluted or dissolved in the selected solvent in the ratio of about 3 to about 25 ml of solvent per gram of acid acceptor. The ratio of the amine to the acid acceptor can vary between 1:0 to about 1:1.1. After addition of the acid acceptor, the reaction mixture can be stirred or allowed to stand from about 8 to about 66 hours, preferably from 10 to 18 hours, at room temperature under a nitrogen stream.

The crude redox releaser can be isolated by distilling off the solvent from the reaction mixture. The residue may be finely milled (if solid); treated with petroleum ether, and washed with solvents such as boiling methanol, petroleum ether, pentane, hexane, and the like; dissolved in a solvent such as methanol, ethanol, warm acetone, cyclohexanone, ether, benzene, tetrahydrofuran or a mixture of solvents such as 7:3 hexane-acetone, or optionally filtered to remove insolubles, and either evaporated to dryness or precipitated in a mixture of ice water and a small amount of mineral acid such as hydrochloric acid. The crude redox releaser can be filtered and washed with a solvent such as water, petroleum ether, pentane, hexane or the like. The product can also be extracted from the ice water-mineral acid mixture with a solvent such as methylene chloride, washed with water, evaporated to dryness, and washed with a solvent, such as petroleum ether. Combinations of the above-described methods of isolation can be employed. In some instances, heating above 40° C. should be avoided.

The crude redox releaser can be purified by liquid chromatography on a column of silica gel using an elution solvent such as 95:5 methylene chloride-methanol, 95:5 methylene chloride-acetone, 96:4 dichloromethanemethanol, 7:3 hexane-acetone, hexane/ethyl acetate (3:2) and the like. Alternatively the crude product can be recrystallized from a solvent such as acetonitrile, dimethylformamide or the like. Combinations of the above methods can be used to purify the isolated redox releaser.

The photographically useful group of some redox releasers have a protective ester function. This protective ester function can be hydrolyzed before purification of the redox releaser, or the redox releaser can retain its protective ester function until ater purification. Hydrolysis of the ester function, before or after purification, can be accomplished by stirring the redox releaser with a solution of a 1 to 5 molar excess of strong alkali such as sodium hydroxide, in deaerated, distilled water under nitrogen at room temperature, or by treating the compound with ammonium or liquid ammonia. Isolation methods used for removing the redox releaser from the hydrolysis reaction mixture are the same as described above for the isolation of the crude redox releaser.

The process of the invention for forming a retained color image in the photographic element is characterized in that (a) a photographic element is exposed imagewise, said element comprising at least one silver halide emulsion layer with which is associated a redox releaser compound corresponding to the above-described formula, (b) the exposed photographic element is processed with an alkaline composition, in the presence of a silver halide developing agent so as to develop the exposed silver halides and, as a function of this development, to oxidize the redox releaser(s) to release a diffusible photographically useful group, such as a dye- or dye precursor, (c) the released photographically useful groups are caused to diffuse into the alkaline processing composition or are caused to migrate onto an image-receiving sheet which is then peeled apart and (d) the developed silver image and the residual silver halides can be removed by a bleach-fix means. A suitable bleach-fix means comprises a bleach-fix cover sheet, as described in U.S. Pat. No. 4,256,826, issued on Mar. 17, 1981.

According to a particularly advantageous embodiment, the photographic film unit of the invention comprises three dye image-providing elements. In a three color system, each silver halide emulsion layer is associated with a dye image-providing material (redox releaser) having its final spectral absorption in a region of the visible spectrum which is that of the sensitivity of the associated silver halide emulsion. The blue-sensitive emulsion layer is associated with a yellow dye-providing material, the green-sensitive emulsion layer is associated with a magenta dye-providing material and the red-sensitive emulsion is associated with a cyan dye-providing material. The dye-providing material associated with each silver halide emulsion layer can be incorporated either in the emulsion layer or in a layer contiguous thereto.

The amount of sulfonamido redox releaser which is used can vary over a wide range depending on the nature of the selected sulfonamido compound and on the results that are desired. For example, layers containing the image-providing sulfonamido compounds can be coated from coating solutions containing from about 0.5% to 8% by weight of the image-providing compound which is distributed in a film-forming and hydrophilic natural or synthetic polymer, such as polyvinyl alcohol or gelatin. This polymer must be able to be permeated by an aqueous alkaline composition such as the one used for processing. The redox releaser compounds can be used at a concentration at least equal to the stoichiometric concentration corresponding to the oxidation reaction of the redox releaser compound with the oxidized developing agent. It is necessary to use at least one mole of redox releaser for two moles of silver halide, but it is desirable to incorporate the redox releaser compound at levels no higher than needed to provide a desirable $D_{max}$.

A silver halide developing agent can be used, provided it produces a cross-oxidation with the image-providing redox releaser compounds corresponding to the above-described formula. The developing agent can be used in the photosensitive element to be activated by the alkaline processing composition. The following developing agents can be used:
hydroquinone,
aminophenols such as N-methyl-p-aminophenol,
Phenidone (1-phenyl-3-pyrazolidone), trademark of Ilford, Ltd.,
Dimezone (1-phenyl-4,4-dimethyl-3-pyrazolidone), trademark of Eastman Kodak Company,
N,N-diethyl-p-phenylenediamine,
3-methyl-N,N-diethyl-p-phenylenediamine,
3-methoxy-N-ethyl-N-ethoxy-p-phenylenediamine,
3-methoxy-N,N-diethyl-p-phenylenediamine, and the like.

The photographic elements and film units of the invention can contain various silver halide emulsion. Useful silver halide emulsions are well known and are described, for example, in *Product Licensing Index*, Vol. 92, December 1971, publication 9232 on page 197, published by Industrial Opportunities Limited, Homewell, Havant Hampshire, P09 1EF, UK.

These emulsions can be chemically and spectrally sensitized, as described on page 107, paragraph III and pages 108–109, paragraph XV in the aforementioned publication. The emulsions can be protected against the production of fog and can be stabilized against loss of sensitivity during keeping, using the material described on page 107, paragraph V, of the aforementioned publication. The emulsions can contain development modifiers, hardeners, coating aids, as described on pages 107, 108, paragraph IV, paragraph VII and paragraph XII of the aforementioned publication. The emulsions may further contain plasticizers, vehicles and filter dyes, such as described in paragraph XI on page 108, in paragraph VIII on page 109 and in paragraph XVI of the aforementioned publication. Moreover, the emulsion layers and the other layers of a photographic product of the invention can contain various addenda which are incorporated using the procedures described on page 109, paragraph XVII, of this same article. Finally, the emulsions can be coated using the various coating procedures mentioned on page 109, paragraph XVIII of this publication.

The support of the photographic elements of the invention can be any material as long as it does not deleteriously affect the photographic properties of the element and is dimensionally stable. Typical flexible sheet materials include cellulose nitrate films, cellulose acetate films, poly(vinyl acetal) films, polystyrene films, poly(ethylene terephthalate) films, polycarbonate films, poly-alpha-olefin films such as polyethylene or polypropylene films, and films of resinous materials. The support is usually about 2 to 6 mils in thickness.

The alkaline processing composition used in the invention is a conventional alkaline solution of an alkaline material such as sodium hydroxide, sodium carbonate or an amine such as diethylamine, preferably having a pH of from 10 to 14. This solution also preferably contains a viscosity increasing agent such as a soluble high molecular weight polymer, a water-soluble cellulose derivative insert to alkaline solutions such as hydroxyethyl cellulose or alkali metal salts of carboxymethyl cellulose such as sodium carboxymethyl cellulose. A concentration of viscosity increasing-agent of about 1% to about 5% by weight of the processing composition will impart thereto a viscosity of about 0.1 Pl to about 200 Pl.

As previously mentioned, the photographically useful groups released from the redox releaser can be diffused into the alkaline processing composition or they can be caused to migrate onto an image-receiving sheet comprising an image-receiving layer on which an image is obtained which is reversed with respect to the redox releaser image retained in the photographic element. If a transferred image is desired, the photographic element can be treated with an alkaline processing composition to effect or initiate development in any manner. A preferred method for applying processing composition is by use of a rupturable container or pod which contains the composition. In general, the processing composition employed in this invention contains the developing agent for development, although the composition could also be just an alkaline solution where the developer is incorporated in the photosensitive element. In such case, the alkaline solution serves to activate the incorporated developer.

The rupturable container employed in this invention can be of the type disclosed in U.S. Pat. Nos. 2,543,181; 2,643,886; 2,653,732; 2,734,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Any material can be used to form the image receiving layer, as long as this material permits mordanting the dye images or fixing them by any other means. The specific material depends, of course, on the dye which is to be mordanted. If acidic dyes are to be mordanted, the image-receiving layer can contain alkaline polymeric mordants such as polymers from amino guanidine or vinylmethylketone derivatives as described in U.S. Pat. No. 2,882,156. Alkaline polymers such as those described in Belgian patent No. 729,202 can also be used as mordants. Other mordants useful in the practice of the invention are, for example, 4-vinylpyridine polymers, 2-vinylpyridine metho-p-toluene sulfonate polymers and similar compounds described in U.S. Pat. No. 2,484,430. Cetyltrimethylammonium bromide can also be used. Effective mordanting compositions are also described in U.S. Pat. Nos. 3,271,147; 3,271,148; 3,704,690 and 3,958,995.

As previously mentioned, for the retained image, after processing with the alkaline composition, it is preferably desirable to remove the silver image and the residual silver halides by processing the photographic element or film unit successively with a bleaching solution to oxidize the silver image, then with a fixing solution to complex and dissolve the oxidized silver image and the residual silver halides. The photographic element or film unit can also be processed with a single bleach-fix solution which comprises both an agent for bleaching of the silver image and an agent for complexing the bleach-oxidized silver and the residual silver halides. An example of bleach-fix solution comprises, in particular, at least one silver oxidizing agent such as the monosodium salt of the ferric complex of ethylenediaminetetraacetic acid and at least one agent complexing the oxidized silver and the residual silver halides, such as an alkali metal or ammonium thiocyanate or thiosulfate.

The bleach-fix treatment can be integral with the photosensitive element. For example, the photosensitive element can be temporarily adhered to a bleach-fix sheet comprising a support containing thereon a bleaching agent and a fixing agent and an overcoat of a timing layer. Between the element and bleach-fix sheet, a rupturable pod containing processing composition can be placed. When the imagewise-exposed element is subjected to pressure, the processing occurs. After a suitable period, the timing layer allows the bleach and fixing steps, and the bleach-fix sheet can be removed to produce the retained image in the element.

According to an alternative embodiment of the image-providing process of the invention, after the bleach-fix step such as previously described, the photographic element or film unit can be processed with an alkaline activator to complete the removal of the diffusible photographically useful material released from the colored redox releaser and to regenerate the initial colors of the residual colored redox releasers which may have been altered by the bleach-fix solution. This processing with an alkaline activator permits a shift toward the final hue of the residual redox releaser colored compounds.

As previously mentioned, a major advantage resulting from the use of substituted sulfonamido redox releaser compounds corresponding to the above-described formula in the photographic elements and film units of the invention, lies in the fact that these redox releasers produce retained color images having stain which is substantially reduced as compared to that obtained with prior art redox releaser compounds.

The term "nondiffusible" as used throughout the specification is intended to mean that the material will not substantially diffuse either within or from the layer in which it is located within the photographic element during contact in an alkaline solution at a pH, for example, of greater than 11. In most cases, the material is ballasted so as to render it nondiffusible. Likewise, the term "diffusible" is intended to mean that the material when in contact with alkaline solution under conditions similar to those described above will substantially migrate from its layer in the photographic element to the image-receiving layer where it is mordanted.

The term "associated with" as used in the specification and claims is understood to mean that the material is either in the same layer with or in a layer adjacent to the material to which it is associated.

The stain can be defined by the following formula:

$$\text{Stain} = D_{min}\tfrac{B}{T} - D_{min}\tfrac{B}{S} - K\left(D_{min}\tfrac{G}{T} - D_{min}\tfrac{G}{S}\right)$$

wherein:

$D_{min}\tfrac{B}{T}$ = overall minimum density read in blue light $D_{min}\tfrac{B}{S}$ = minimum density read in blue light and due to the support. For usual transparent supports, this value is substantially equal to 0.03.

-continued $K$ = percentage of undesirable absorption in blue peculiar to each dye.

For most of the magenta dyes described in the examples below, this factor K is in the range from 0.20 to 0.25.

$D_{min} \frac{G}{T}$ = overall minimum density read in green light $D_{min} \frac{G}{S}$ = minimum density read in green light and due to the support. For usual transparent supports, this value is substantially equal to 0.03.

The following examples further illustrate the invention:

EXAMPLE 1

Preparation of 3,4,6-trimethyl-5-[3-(1-hydroxy-5-methanesulfonamido-4-naphthylazo)-benzenesulfonamido]-N,N-didodecyl-salicylamide

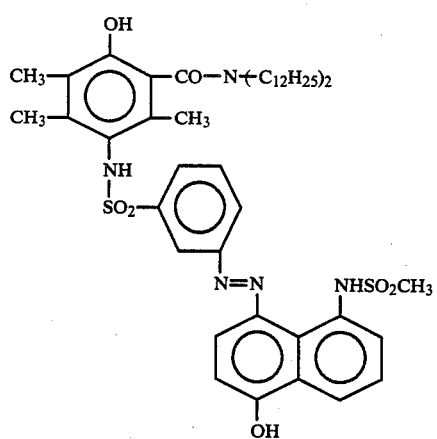

This magenta redox releaser compound was prepared in six steps (1) to (6) described hereafter.

STEP (1)

Preparation of 2-hydroxy-3,4,6-trimethylbenzoic acid

This product was prepared from 2,3,5-trimethylphenol by Kolbe's reaction.

STEP (2)

Preparation of 2-hydroxy-3,4,6-trimethylbenzoic acid phenylester

In a 500 ml three-necked flask fitted with a mechanical stirrer, a reflux condenser connected to a water pump to absorb the gaseous hydrochloric acid formed during the reaction, and a dropping funnel, were placed 200 ml of dry toluene and 54 g (0.3 mole) of 2-hydroxy-3,4,6-trimethylbenzoic acid prepared in step (1), and 56.4 g (0.6 mole) of phenol were added. The mixture was heated at 100° C. until the reagents were completely dissolved. 27 ml of phosphorus oxychloride were then added dropwise over 30 minutes, and the mixture was refluxed (110° C.) for 8 hours. A substantial evolution of gaseous hydrochloric acid took place. The mixture was cooled to 80° C. and 150 ml of water were added. The aqueous layer was decanted, and the organic layer was washed a second time with an aqueous solution of sodium bicarbonate. The aqueous layer was decanted and the toluene solution was dried with anhydrous magnesium sulfate. The solution was filtered, and the toluene solvent was distilled off. The residue was dissolved in 90 ml of boiling isopropanol and the desired product crystallized upon cooling. 38 g of a white product were obtained (M.P.=74° C.).

STEP (3)

Preparation of N,N-didodecyl-2-hydroxy-3,4,6-trimethylbenzamide

In a 250 ml flask fitted with a mechanical stirrer and a reflux condenser, were placed 30.7 g (0.12 mole) of the 2-hydroxy-3,4,6-trimethylbenzoic acid phenyl ester prepared in step (2) and 42.36 g (0.12 mole) of didodecylamine. This mixture was heated in a nitrogen atmosphere at 120° C. for 12 hours. The phenol formed was distilled off under vacuum (7 g were thus collected). After cooling, the crystallization of the desired product was started by scraping.

The precipitate formed was filtered and recrystallized from acetonitrile (5 ml of acetonitrile for 1 g of product). The white crystals were filtered (56 g, i.e. a yield of 91%) and vacuum dried (M.P.=56° C.).

STEP (4)

Preparation of N,N-didodecyl-3,4,6-trimethyl-5-(paramethoxy-phenylazo)salicylamide (a) Preparation of the diazo compound of p-anisidine 12.3 g (0.1 mole) of p-anisidine were dissolved in a solution comprising 100 ml of water and 32.4 ml of concentrated hydrochloric acid. The p-anisidine hydrochloride solution was cooled to 0° C. and 7 g of sodium nitrite in 10 ml of water were added dropwise with stirring while cooling. Stirring was continued for 2 hours, the temperature being maintained at 0° C.

(b) Coupling reaction

A solution comprising 51.5 g of N,N-didodecyl-2-hydroxy-3,4,6-trimethylbenzamide prepared in step (3), 400 ml of tetrahydrofuran and 40 ml of a 30% aqueous solution sodium hydroxide was cooled to a temperature in the range of from 0° C. to 5° C.

This solution was stirred and the diazonium salt solution prepared in (a) was added dropwise. A red dye was formed and stirring was continued overnight at 0° C.-5° C. The pH was then adjusted to 6 with acetic acid and an orange dye precipitated. The precipitate was filtered off, dried and recrystallized from isopropanol (1 g of dye for 8 ml of isopropanol). 58 g of pure dye were obtained, i.e., a yield of 90% (M.P. 94° C.).

STEP (5)

Preparation of N,N-didodecyl-3,4,6-trimethyl-5-aminosalicylamide

In a hydrogenation autoclave was placed a solution of 26 g (0.04 mole) of the dye of step (4) in 350 ml of isopropanol and 2 g of 10% palladium on charcoal. The dye was reduced under a hydrogen pressure of 980 kPa at a temperature of from 50° C. to 60° C. At the end of hydrogenation, the catalyst was filtered off, the solvent was distilled off under reduced nitrogen pressure and the crude product was filtered off. The product was recrystallized a first time in the minimum amount of ethyl acetate after being discolored with animal charcoal, and recrystallized a second time from acetonitrile (1 g of product for 10 ml of acetonitrile). 15 g of pure beige crystals were obtained, i.e., a yield of 71% (M.P.=90° C.).

STEP (6)

Preparation of the magenta redox releaser compound: 3,4,6-trimethyl-5-[3-(1-hydroxy-5-methanesulfonamido-4-naphthylazo)-benzenesulfonamido]-N,N-didodecyl-salicylamide In a 500 ml flask fitted with a mechanical stirrer, a reflux condenser, a nitrogen inlet and a dropping funnel, was placed a solution of 10.60 g (0.02 mole) of N,N-didodecyl-3,4,6-trimethyl-5-aminosalicylamide prepared in step (5) in 80 ml of anhydrous tetrahydrofuran. A solution of 10.23 g of 1-carbethoxyoxy-5-methanesulfonamido-4-naphthyl-azobenzene-3'-sulfochloride in 150 ml of anhydrous tetrahydrofuran was then added dropwise with stirring. Stirring was continued for 3 hours at room temperature, and a solution of 1.60 g (0.02 mole) of anhydrous pyridine in anhydrous tetrahydrofuran was added. Stirring was continued for 24 hours at room temperature under a nitrogen stream. The solvent was then distilled off and the crude 1-carbethoxyoxy compound was finely milled.

The protective ester function of the naphthol function was hydrolyzed with an alkaline solution prepared as follows. Distilled water was boiled for 3 hours under a nitrogen stream. After cooling, 2.1 g of sodium hydroxide was added to 30 ml of the previously prepared deaerated distilled water.

The crude 1-carbethoxy compound was added by small fractions to the alkaline solution swept with a nitrogen stream, and the mixture was stirred for 2 hours at room temperature. The mixture was then poured over cracked ice containing hydrochloric acid, the crude magenta redox releaser compound was filtered off, washed with deaerated distilled water, and vacuum dried. The compound was purified by liquid chromatography on a column of silica gel, the elution solvent being a mixture of 95:5 methylene chloride-methanol 7 g of pure magenta redox releaser compound were thus collected.

The measured redox potential was:
$E_{\frac{1}{2}} = -170$ mV at pH=14
$E_{\frac{1}{2}} = -50$ mV at pH=11.5

EXAMPLE 2

Preparation of 3,4,6-trimethyl-5[4-(4-hydroxy-3-chlorophenylazo)-benzenesulfonamido]-N,N-didodecyl-salicylamide

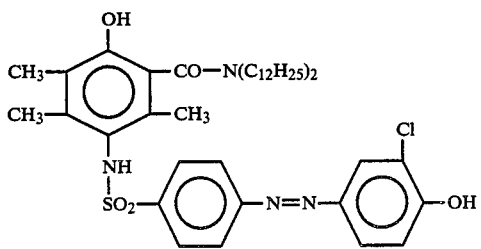

This yellow redox releaser compound was prepared in six steps, the first five steps being such as described in example 1, the sixth step being described hereafter.

In a 500 ml flask fitted with a mechanical stirrer, a reflux condenser and a nitrogen inlet, was placed a solution of 10.60 g (0.02 mole) of N,N-didodecyl-3,4,6-trimethyl-5-aminosalicylamide prepared in step (5) of example 1, in 100 ml of anhydrous tetrahydrofuran.

To this solution stirred under a nitrogen stream was added a solution of 7.5 g of 1-acetoxy-2-chloro-4-phenylazo-benzene-4'-sulfochloride in 30 ml of anhydroux tetrahydrofuran. Stirring was continued for 2 hours at room temperature. A solution of 1.6 g of anhydrous pyridine in 5 ml of anhydrous tetrahydrofuran was added. Stirring was continued overnight under a nitrogen stream. The solvent was distilled off and 8 g of crude 1-acetoxy compound was collected and purified by liquid chromatography on a column of silica gel, the elution solvent being a mixture of 95:5 methylene chloride-acetone. 7.35 g of pure 1-acetoxy compound were thus obtained.

The protective ester function of the phenol function was hydrolyzed by treating the 1-acetoxy compound in liquid ammonia. 6.45 g of this pure yellow redox releaser compound were collected.

Redox potential: $E_{\frac{1}{2}} = -250$ mV at pH=14.

EXAMPLE 3

Preparation of 1-hydroxy-3-methyl-4-[3-(1-carbethoxyoxy-5-methanesulfonamido-4-naphthylazo)-phenylsulfonamido]-N-[4-(2,4-ditert-amyl-phenoxy)butyl]-2-naphthamide

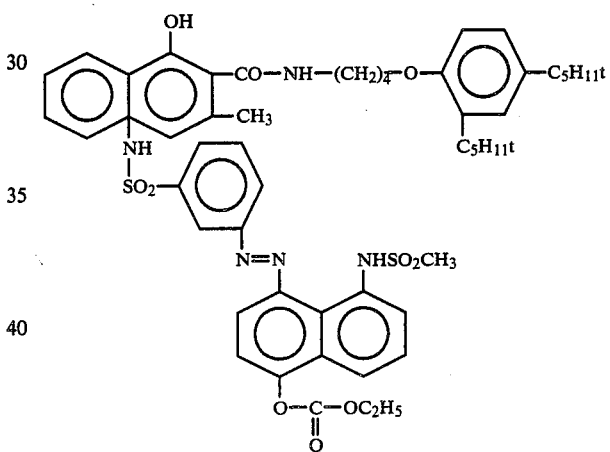

This magenta redox releaser compound was prepared in ten steps described hereafter.

STEP (1)

Preparation of 1-phenyl-2-propanol

In a 4 liter three-necked flask fitted with a mechanical stirrer and a reflux condenser, were placed 1500 ml of water, 150 g of sodium hydroxide (pellets), 190 ml of ethanol and 180 g of phenylacetone. The mixture was stirred and heated to 80° C., and 150 g of Raney alloy was added very cautiously by small amounts over about 1 hour. During the addition, heating was discontinued and the temperature was maintained at 85°-87° C.

After the addition was complete, the mixture was heated for 30 minutes at 85° C. The mixture was cooled, filtered, the alcohol solvent evaporated in a rotary evaporator under reduced pressure, and the remaining aqueous phase was extracted three times with 400 ml of ether. The ether extracts were dried over anhydrous sodium sulfate, evaporated and distilled. 155 g of a colorless liquid were obtained. Boiling point (9 mm Hg)=92° C. $n_D^{23} = 1.5198$. Yield=85%

STEP (2)

Preparation of 1-phenyl-2-propanol p-toluene sulfonate

In a 1 liter three-necked flask fitted with a stirrer and calcium chloride trap, were placed 68 g of 1-phenyl-2-propanol prepared for Step (1) in 100 ml of pyridine. A solution of 95 g of para-toluene sulfonyl chloride in 250 ml of pyridine was added dropwise at a temperature below 5° C. The reaction vessel was left in a brine bath for 65 hours with stirring.

The solution was poured into 4 to 5 volumes of water and ice. The solid which precipitated was filtered and redissolved in 400 ml of chloroform. The chloroform solution was washed twice with water, dried over anhydrous sodium sulfate filtered and evaporated to dryness 138 g of crude product in the form of a white powder were obtained.

The crude product was recrystallized from 650 ml of cyclohexane.

128 g of a white solid melting at 93° C. were collected. Yield=88%.

STEP (3)

Preparation of ethyl-2-carboxyethyl-3-methyl-4-phenyl-1-butyrate 0.91 mole of sodium ethylate was prepared by reacting 21 g of sodium with 450 ml of ethanol. When all the sodium had disappeared, 145 g of ethyl malonate were added while heating (70° C.). The resulting solution was then evaporated to dryness in a rotary evaporator. The solid residue was dissolved in 400 ml of dry DMA. This solution was then poured into a 2 liter three-neck flask fitted with a stirrer, a reflux condenser and a thermometer. Then 264 g of the sulfonic ester prepared in Step (2) were added and the mixture was heated at 70° C. for 15 hours with stirring. Three volumes of ether were added to the cooled solution and the suspended solid was filtered and washed with ether. The filtrate was evaporated to dryness and extracted with 600 ml of chloroform. The chloroform phase was washed twice with water, dried over anhydrous sodium sulfate, evaporated to dryness and distilled.

1st fraction: 138° C./0.6 mm Hg $n_D^{23}$=1.488 (100 g)
2nd fraction: 141° C./1 mm Hg $n_D^{23}$=1.490 (102 g)
Total: 202 g Yield=73%

STEP (4)

Preparation of 2-carboxyethyl-3-methyl-4-phenyl-1-butyric acid

In a liter three-necked flask fitted with a stirrer, a thermometer and a dropping funnel, were placed 89 g (0.32 mole) of the diethyl ester prepared in Step (3) in 260 ml of ethanol, and and aqueous solution of 21 g of potassium hydroxide was added dropwise over 1 hour at room temperature. The mixture was stirred for 4½ hours at room temperature. The ethanol was then evaporated under vacuum, the temperature in the water bath never rising above 30° C. The remaining oil was dissolved in 400 ml of water acidified to pH 3 with acetic acid (if necessary, acid is again added until no more turbidity is observed). The solution was extracted three times with 200 ml of ether. The ether extracts were washed twice with 300 ml of water.

The ether phase was dried over anhydrous sodium sulfate, evaporated to dryness, and dried by two azeotropic distillations with 100 ml of anhydrous benzene under a pressure of about 700 mm Hg. The last traces of benzene were distilled off under a higher vacuum.

71 g of amber-colored oil were obtained. Yield=89%.

STEP (5)

Preparation of 2-carboxyethyl-3-methyl-1-tetralone (a) Preparation of the acid chloride In a 1 liter three-necked flask fitted with a stirrer, dropping funnel, a thermometer and a calcium chloride trap, were placed 200 ml of ether dried over sodium, 38 ml of newly distilled thionyl chloride, 40 drops of pyridine (analytical grade) and 12 drops of dimethylformamide.

A solution of 71 g (0.28 mole) of the acid prepared in Step (4) in 80 ml of anhydrous ether was then added rapidly at room temperature. The resulting solution was left for 3 hours at room temperature, and heated for 20 minutes at 30°–40° C. The ether solvent was evaporated and the residue was dried by twice distilling with 50 ml of anhydrous benzene. The benzene was evaporated under vacuum at 30°–40° C. for 30 minutes 78 g of acid chloride were obtained as an oil which began to crystallize.

(b) Ring forming reaction

The 78 g of previously obtained oil were dissolved in 500 ml of sodium desiccated benzene and poured into a 1 liter three-necked flask fitted with a stirrer, a dropping funnel, a thermometer and a calcium chloride trap. This solution was cooled to 4° C., and a solution of 86 g of tin tetrachloride in 150 ml of anhydrous benzene was added dropwise at a temperature below 5° C. The reaction vessel was allowed to stand for 12 hours in brine and for 6 hours at room temperature. The reaction mixture was then poured over 300 g of cracked ice, the benzene layer was decanted, and washed twice with water, once with a solution of sodium bicarbonate, and once again with water. The benzene phase was dried over sodium sulfate, evaporated to dryness and distilled.

49 g of a slightly yellow oil were collected at 128° C./0.7 mm Hg. Yield=74%.

STEP (6)

Preparation of ethyl-1-hydroxy-3-methyl-2-naphthoate

To a solution of 150 g of 2-carbethoxy-3-methoxy-1-tetralone prepared in Step (5) in 350 ml of decahydronaphthalene were added 75 g of catalyst (5% palladium on carbon) The air of the flask was expelled and the mixture was heated at 160° C. Rapid evolution of hydrogen gas occurred. After heating for 2 hours 15 min, the evolution of hydrogen slowed and a total of 6.210 liters of hydrogen was collected. The mixture was cooled, the catalyst was filtered off and washed with a large volume of acetone. The filtrate and the acetone were combined and evporated to dryness.

This residue was distilled under a vacuum. Two fractions were collected.

I B.P. 124° C. 0.2 to 0.4 mm Hg 43 g
II B.P. 124°–134° C. 0.2 mm Hg 54 g

Fraction I, which was pasty, was recrystallized from pentane, 15 g of a first crop were thus separated: M.P.=62° C. and 5 g of a second crop, M.P.<50° C.

Fraction II was also recrystallized from pentane and supplied 42 g of a well crystallized white compound: M.P.=66° C.

By repeated recrystallizations from pentane, a pure sample (according to elementary analysis) was obtained: M.P.=68° C. whose structure was confirmed by NMR.

Both recrystallized fractions, i.e., 57 g, correspond to a yield of 38%.

STEP (7)

Preparation of N-[4(2,4-ditertioamyl-phenoxy)butyl]-1-hydroxy-3-methyl-2-naphthamide A mixture of 57.5 g of ethyl-1-hydroxy-3-methyl-2-naphthoate prepared in Step (6) and 84 g of 2,4-ditertamylphenoxybutylamine was heated at 140° C. for 10 hours with nitrogen bubbling. The mixture was cooled and dissolved in 800 ml of pentane. Crystals appeared gradually and, after allowing the mixture to stand for 2 hours, the abundant white precipitate was filtered off. Thus 40 g of a product melting at 90° C. were obtained.

The filtrate was evaporated to dryness. The resulting residue was heated again with nitrogen bubbling for 7 hours, cooled and again diluted with 800 ml of pentane. Crystals appeared and, after allowing the mixture to stand for 2-3 hours at room temperature, the product was filtered off. Thus 25 g of amide were collected.

Both batches were combined and washed with 150 ml of petroleum ether. Thus 59 g of amide were obtained, M.P.=90° C., which corresponded to a yield of 48%.

A pure sample (according to elementary analysis) obtained by crystallization in cyclohexane melted at 93.6° C. Elementary analysis and NMR confirmed the structure.

Step (8)

Preparation of 1-hydroxy-3-methyl-4-(p-methoxyphenylazo)-N-[4-(2,4-di-5-amyl-phenoxy)-butyl]-2-naphthamide (a) Diazotation of p-anisidine In a 250 ml three-necked flask were placed 35 ml of water, 41 ml of concentrated hydrochloric acid. 17.2 g of p-anisidine were added with stirring while maintaining the temperature below 25° C.

9.75 g of $NaNO_2$ were then added in small amounts while maintaining the temperature below 5° C. The mixture was allowed to stand for 1 hour at 0° C.

(b) Coupling reaction 58 g of the product of step (7) were dissolved in a mixture of 180 ml of pyridine and 90 ml of dimethyl formamide. The diazo salt solution was added dropwise to this solution stirred at a temperature below 10° C. Stirring was continued overnight at a temperature of about 0° C.

The dye was crystallized slowly as about 100 ml of methanol were added. When crystallization was duly initiated 80 ml of water were added. The mixture was stirred for several hours, filtered and dried. 65 g of crude dye were recrystallized from 1 liter of acetonitrile. 51 g of collected product corresponded to a yield of 68%.

STEP (9)

Preparation of 1-hydroxy-3-methyl-4-amino-N-[4-(2,4-ditert-amyl-phenoxy)butyl]-2-naphthamide A suspension of 51 g of the azo dye prepared in step (9) in 1.2 liter of ethanol was hydrogenated under normal pressure in the presence of 3 g of 5% platinum on carbon. The reaction mixture was heated to about 40° C. to initiate reduction, which was continued at room temperature (25° C.). In the course of the reduction the amino derivative precipitated gradually in the form of a slightly colored product. The reaction mixture was cooled, and the product filtered off. The resulting compound was recrystallized from $CH_2Cl_2$. 26 g were obtained. M.P.=190° C.

A second crop of 8 g was obtained by concentrating the filtrate and recrystallizing from $CH_2Cl_2$. 34 g were thus obtained, i.e. a yield of 82.4%

The structure of a sample obtained by repeated crystallizations was confirmed by NMR, IR and elementary analysis.

STEP (10)

Preparation of 1-hydroxy-3-methyl-4-[3-(carbethoxy-oxy-5-methanesulfonamido-4-naphthylazo)phenylsulfonamido]-N-[4(2,4-di-5-amylphenoxy)butyl]-2-naphthamide 25.2 g of the aminonaphthol compound of step (9) and 29.4 g of 1-carbethoxyoxy-4-(3-chlorosulfonylphenylazo)-5-methanesulfonamidonaphthalene were dissolved in 500 ml of anhydrous methylene chloride. The solution was allowed to stand under nitrogen at room temperature for 48 hours. 2.4 g of pyridine were added and the mixture was again allowed to stand for 24 hours. The reaction mixture was evaporated to dryness under vacuum, extracted with 300 ml of hot acetone, and filtered to remove the insoluble portion. The filtrate was again evaporated to dryness under vacuum.

28.4 g of magenta redox releaser compound were obtained which retained its protective function, i.e., a yield of 58%.

EXAMPLE 4

Preparation of 1-hydroxy-3-methyl-4-[3-(1-hydroxy-5-methanesulfonamido-4-naphthylazo)phenylsulfonamido]-N-didodecyl-2-naphthamide

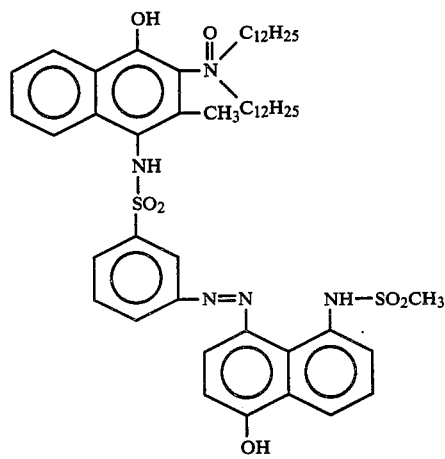

This magenta redox releaser compound was prepared in ten steps, the first six steps being such as described in example 3, steps (7) to (10) being described hereafter.

STEP (7)

Preparation of N-(di-n-dodecyl)-1-hydroxy-3-methyl-2-naphthamide

A solution of 29 g of the ethyl ester prepared in step (6) of example 3 and 45 g of didodecylamine in 500 ml of decane was refluxed while distilling very slowly for about 6 hours. The reflux temperature settled at 174° C. and the 100 ml of distillate carried away a portion of the alcohol released during the reaction.

The hexane was vacuum evaporated and an oily residue was obtained which crystallized upon cooling. 59 g of amide were obtained after recrystallization from acetone, which corresponds to a yield of 87%.

The purity of the compound was established by differential thermal analysis. Very narrow peak at M.P.=63° C. TLC: Rf=0.7 with a mixture of 7:3 hexane-acetone.

STEP (8)

Preparation of N-didodecyl-1-hydroxy-3-methyl-4-(4-methoxyphenylazo)-2-naphthamide A solution of 4-methoxy-phenyl-diazonium chloride was prepared by adding dropwise at 0° C. a solution of 1.8 g of sodium nitrite dissolved in 2.5 ml of water to a solution of 3.075 g of p-anisidine dissolved in 25 ml of water and 8.1 ml of concentrated hydrochloric acid. The reaction mixture was allowed to stand for 2 hours.

This solution was added slowly to a solution of 11.7 g of the amide prepared in step (7) dissolved in a mixture of 95 ml of tetrahydrofuran and 7.25 ml of 50% sodium hydroxide, the temperature being kept below 5° C. After stirring overnight, the product precipitated in an aqueous solution containing 50 ml of HCl and 500 ml of water. The mixture was allowed to stand for several hours and the solid was separated by filtration on a Buchner funnel. The product was dried and recrystallized from acetone. 11.3 g were thus collected, i.e., a yield of 77%.

STEP (9)

Preparation of N-didodecyl-1-hydroxy-3-methyl-4-amino-2-naphthamide 33.5 g of the azo dye prepared in step (8) suspended in 600 ml of ethanol was reduced by hydrogen under normal pressure in the presence of 2 g of 5% platinum on carbon. The reduction was carried out at room temperature, the dye being gradually dissolved and replaced by a gray precipitate. After the reduction was complete, the amine was dissolved in pyridine without heating, and the catalyst was filtered off. The filtrate was evaporated to dryness at room temperature.

The compound was used in its crude form and was stored in a refrigerator under nitrogen.

18.7 g were obtained, i.e. a yield of 68%.

STEP (10)

Preparation of 1-hydroxy-3-methyl-4-[3-(1-hydroxy-5-methanesulfonamido-4-naphthylazo)phenylsulfonamido]-N-didodecyl-2-naphthamide 27.5 g of the aminonaphthol prepared in step (9) and 29.15 g of 1-carbethoxy-oxy-4-(3-chlorosulfonylphenylazo)-5-methanesulfonamidonaphthalene were dissolved in 800 ml of anhydrous methylene chloride. The solution was allowed to stand under nitrogen at room temperature for 48 hours. 2.4 g of pyridine were added and the mixture was again allowed to stand for 24 hours. The reaction mixture was evaporated to dryness under vacuum. The residue was dissolved by refluxing in 300 ml of a 7:3 by weight hexane-acetone mixture, filtered to remove the insoluble portion and again evaporated to dryness under vacuum, avoiding heating above 40° C. The residue was chromatographed twice on a silica column, using a mixture of 7:3 by weight hexane-acetone as the eluent.

The fractions containing the desired product were evaporated to dryness under vacuum. 22 g of the protected sulfonamido dye (1-carbethoxyoxy derivative) were thus obtained as a yellow product, which corresponded to a yield of 43%.

HYDROLYSIS OF THE PROTECTIVE FUNCTION

The 22 g of protected dye prepared above were dissolved in 180 ml of acetone with vigorous stirring under nitrogen. At room temperature (25° C.), 60 ml of a 10% sodium hydroxide solution prepared from water deaerated by prolonged boiling was added. The reaction mixture was stirred for 1½ hours and poured into an ice-water mixture to which the stoichiometric amount plus a 10% excess of hydrochloric acid had been added. The precipitated product was filtered off and dried under vacuum at room temperature. The product was recrystallized slowly from 400 ml of acetonitrile and dried under vacuum. 16.8 g of the compound were thus obtained. Purity was confirmed by TLC and LPC analysis. The final yield was 35%.

EXAMPLE 5

Preparation of 1-hydroxy-3-methyl-4-[4-(1-hydroxy-2-(N-t-butylsulfamoyl)-5-methanesulfonamido-4-naphthylazo)-phenylsulfonamido]-N-[(2,4-ditert-amyl)phenoxy-4-butyl]-2-naphthamide

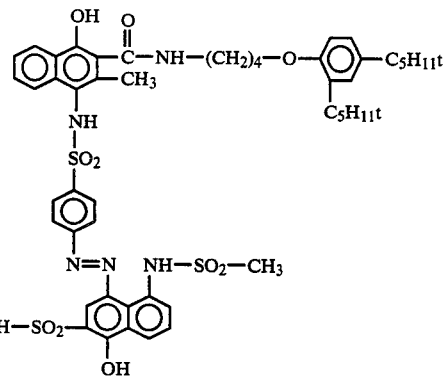

The magenta redox releaser compound was prepared by reacting the aminonaphthol prepared in step (9) of example 3 with 2-(N-tert-butylsulfonamido)-4-(4-chlorosulfonylphenylazo)-5-methylsulfamoyl-1-naphthol, according to the following procedure:

To a solution of 20.2 g of the aminonaphthol derivative, prepared in step (9) of example 3, in 200 ml of dry pyridine at 0° C., was added with stirring and under nitrogen 25.2 g (a 10% molar excess) of 2-(N-t-butylsulfonamido)-4-(4-chlorosulfonylphenylazo)-5-methylsulfonamoyl-1-naphthol. The mixture was stirred for 2 hours at a temperature below 10° C., followed by stirring overnight at room temperature. The solution was poured into 3 liters of ice water containing 200 ml of concentrated hydrochloric acid. The dye which precipitated was filtered, washed with a large volume of water and dried under vacuum. The dye was recrystallized twice from acetonitrile, yielding 13.9 g of product (33.5% yield).

lized from 200 ml of acetonitrile to yield 4.5 g of pure magenta redox releaser compound (M.P.=167° C.).

EXAMPLE 7

Preparation of 1-hydroxy-2-propyl-3-phenyl-4(2(5-methanesulfonamido-1-hydroxy)naphthylazo-3-benzene sulfonamido]-7-[(2,4-ditert-amyl)phenoxy acetyl]naphthamide

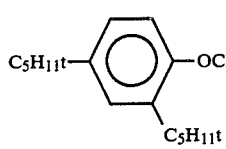 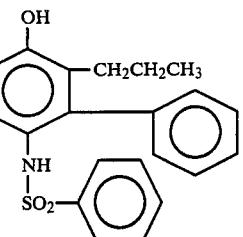 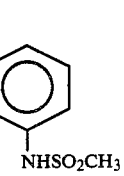

This redox releaser compound was prepared in nine steps (1) to (9) described hereinafter.

STEP (1)

Preparation of 1-(4-Nitro)-phenylacetoxy-3-phenyl-7-nitro-naphthalene

This compound was prepared by adapting the method described by G. Henseke, H. Schiefer, C. Kipping and K. Schonfelder (D. D. R. Patentschrift 71770 of Mar. 20, 1970).

A mixture consisting of 315 g of para-nitrophenylacetyl chloride, 96.5 g of phenylacetylene and 1700 ml of xylene was heated for 8 hours with good stirring at reflux temperature. The equipment was protected from moisture. After 5 hours, crystals begin to appear in the solution during heating. After cooling the reaction mixture, the crystals were filtered off, washed with petroleum ether and dried. If necessary, recrystallization is possible in xylene.

Obtained: 300 g—Yield: 88% Yellow crystals M.P.=215° C.

STEP (2)

Preparation of 3-Phenyl-7-nitro-1-naphthol 270 g of 1-(4-Nitro)-phenylacetoxy-3-phenyl-7-nitro-naphthalene prepared in step (1) were dissolved in a solution of 180 g of potassium hydroxide in 1700 ml of methanol. The solution thus obtained was refluxed for 10 minutes. After cooling, concentrated hydrochloric acid was added in an amount sufficient to render the mixture just acidic. The methanol was evaporated off under reduced pressure and the residue was dissolved in ethyl ether. The ethyl ether solution was extracted repeatedly with saturated aqueous solutions of sodium bicarbonate until the para-nitrophenylacetic acid formed during the hydrolysis was completely removed. Finally the ether extract was washed with water, dried and evaporated under reduced pressure. The residue was washed with petroleum ether and the crystals formed were filtered off and dried.

EXAMPLE 6

Preparation of 1-hydroxy-3-phenyl-4-[4-(1-hydroxy-2-N-tert-butyl-sulfamoyl-5-methanesulfonamido-4-naphthylazo)-phenylsulfonamido]-N-didodecyl-2-naphthamide

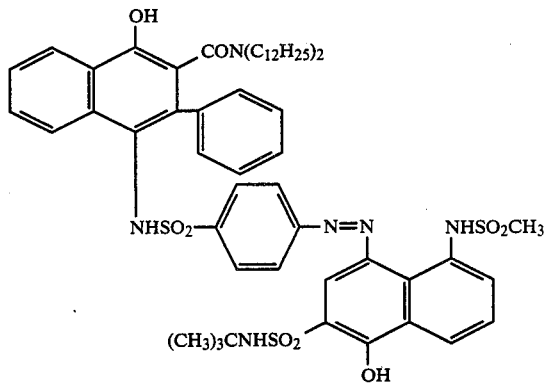

This magenta redox releaser compound was prepared according to the following procedure:

To a solution of 9.0 g (0.015 mole) of N-didodecyl-1-hydroxy-3-phenyl-4-amino-2-naphthamide in 50 ml of pyridine at 0° C. were added 10.53 g (0.0188 mole) of 4-(1-hydroxy-2-N-tert-butylsulfamoyl-5-methanesulfonamido-4-naphthylazo)-phenylsulfochloride. The mixture was stirred under nitrogen at 0° C. for 1 hour. The mixture was evaporated to low volume, and the residue was dissolved in 50 ml of methanol and poured with vigorous stirring into 500 ml of ice water containing 50 ml of concentrated hydrochloric acid. The magenta precipitate was filtered and dried to yield 14.25 g of crude redox releaser. The product was warmed with 500 ml of ethyl acetate and 2.25 g of insoluble material was removed from the desired product by filtration. The solvent was evaporated, and the crude product was purified by dry column chromatography using 96:4 dichloromethanemethanol. The product was recrystal- Obtained: 125 g Yield: 75% Red orange crystals M.P.=195° C.

STEP (3)

Preparation of 1-Allyloxy-3-phenyl-7-nitronaphthalene

A mixture of 125 g of 3-phenyl-7-nitro-1-naphthol prepared in step (2), 65 g of anhydrous potassium carbonate, 95 g of allyl bromide and 1200 ml of acetone was refluxed for 4 hours with good stirring. After cooling, the mineral salts were removed by filtration and the residual organic solution was evaporated to dryness under reduced pressure. The crystals thus formed were washed with petroleum ether, filtered and dried at 80° C. under reduced pressure.

Obtained: 128.5 g Yield: 89% Light yellow crystals M.P.: 134° C.

STEP (4)

Preparation of 2-Allyl-3-phenyl-7-nitro-1-naphthol 31 g of 1-Allyloxy-3-phenyl-7-nitro-naphthalene prepared in step (3) were gradually heated to 180° C. in 390 ml of decaline, the solution being stirred and maintained under nitrogen. The temperature of 180° C. was maintained for about 1 hour. After cooling, the crystals formed were washed with petroleum ether, filtered off and dried at 80° C. under reduced pressure.

Obtained: 29 g Yield: 94% Yellow crystals MP=146° C.

STEP (5)

Preparation of 2-Propyl-3-phenyl-7-amino-1-naphthol 14 g of 2-Allyl-3-phenyl-7-nitro-1-naphthol prepared in step (4) were dissolved in 200 ml of acetone. 300 ml of ethanol and one pinchful of a 10% palladium on charcoal catalyst were added. The resulting mixture was hydrogenated at room pressure and temperature until the theoretical amount of hydrogen was absorbed. The catalyst was then removed by filtration and the residual solution was evaporated to dryness under reduced pressure. The resulting crystals were washed with petroleum ether, filtered off and dried under sulfuric vacuum.

Obtained: 25 g Yield: 95% White crystals M.P.=160° C.

STEP (6)

Preparation of 1-Hydroxy-2-propyl-3-phenyl-7[(2,4-ditert-amyl)-phenoxyacetyl]naphthamide To a solution of 20 g of 2-Propyl-3-phenyl-7-amino-1-naphthol prepared in step (5) in 300 ml of acetone and 16 ml of diethylaniline, was added 15.5 g of (2,4-ditert-amyl)phenoxyacetyl. The resulting solution was stirred for 1 hour at reflux temperature under nitrogen. The reaction mixture was poured into about 700 ml of ice water containing enough hydrochloric acid to render the mixture acidic. The organic products were extracted with ethyl ether. The extracts were washed with water, dried and evaporated to dryness under reduced pressure. After treating the residue with petroleum ether, the resulting crystals were filtered off. The crude material was recrystallized in 200 ml of "essence E" (a cut of hydrocarbon distillation consisting mainly of nonane).

Obtained: 24 g Yield: 59% White crystals M.P.=159° C.

STEP (7)

Preparation of 1-Hydroxy-2-propyl-3-phenyl-4-[(4-carboxy)-phenylazo]-7-[(2,4-ditert-amyl)phenoxyacetyl]naphthamide (a) Preparation of the diazo compound 1.51 g of para-aminobenzoic acid were dissolved in 11 ml of N sodium hydroxide. 11 ml of a normal solution of sodium nitrite in water were added to the preceding solution. The mixture was then added slowly to 28.5 ml of normal hydrochloric acid, while maintaining the temperature below 5° C.

(b) Coupling reaction

The diazo compound prepared as above was added over 10 minutes to a solution consisting of 5.51 g of 1-Hydroxy-2-propyl-3-phenyl-7-[(2,4-ditert-amyl)-phenoxyacetyl]naphthamide prepared in step (6) and 50 ml of a 2M solution of potassium hydroxide in methanol. The mixture was stirred for 2 hours at a temperature of about 10° C. The organic solvents were then removed by evaporation under reduced pressure. The residue was dissolved a water-methylene chloride mixture. The organic phase was decanted, washed with water, dried and evaporated to dryness under reduced pressure. The residue was washed with petroleum ether and the crystals formed were filtered and dried.

Obtained: 6.1 g Yield: 87% Orange crystals M.P.=198° C. (dec)

Spectral data: $\epsilon 521 = 30\ 000$ (KOH 0.1M in MeOH)
$\epsilon 453 = 28\ 000$ (AcOH 0.1M in MeOH)

STEP (8)

Preparation of 1-Hydroxy-2-propyl-3-phenyl-amino-7[(2,4-ditert-amyl)phenoxyacetyl]naphthamide A suspension of 6.15 g of 1-Hydroxy-2-propyl-3-phenyl-4-[(4-carboxy)phenylazo]-7-[(2,4-ditertamyl)-phenoxyacetyl]naphthamide prepared in step (7) in 100 ml of ethanol was refluxed under nitrogen with strong stirring. A solution of 6.93 g of sodium hydrosulfite in 36 ml of water was then added. The reaction mixture was stirred for 30 minutes at reflux temperature. After cooling, the reaction mixture was poured into 200 ml of ice water. The organic products were extracted with ethyl ether. The extracts were washed with a sodium bicarbonate saturated aqueous solution and with water. They were finally dried and evaporated to dryness under reduced pressure. After treatment with petroleum ether, the crystals formed were filtered off. The crude product was recrystallized from acetonitrile. The recrystallized product was washed with boiling methanol and with petroleum ether before being dried.

Obtained: 4.5 g Yield: 90% White crystals

STEP (9)

Preparation of 1-Hydroxy-2-propyl-3-phenyl-4[2(5-methanesulfonamido-1-hydroxy)naphthylazo-3-benzenesulfonamido]-7-[(2,4-ditert-amyl)phenoxy acetyl]naphthamide The three following solutions were mixed and left in contact for 66 hours under nitrogen atmosphere:

3.8 g of 1-hydroxy-2-propyl-3-phenyl-4-amino-7[(2,4-ditert-amyl)phenoxyacetyl)]naphthamide prepared in step (8) in 60 ml of methylene chloride, 4.1 g of (2-naphthylazo-5-methanesulfonamido-1-ethoxycarbonyloxy)-3-benzene sulfonyl chloride in 60 ml of methylene chloride, 0.54 g of pyridine in 13.5 ml of methylene chloride.

The solvent was removed under reduced pressure and the residue was treated with petroleum ether. The crystals formed were filtered, washed with boiling methanol, washed with petroleum ether and dried.

Obtained: 5.5 g Yield=79% Red crystals M.P.=168° C. (dec.)

HYDROLYSIS REACTION 5.5 g of the preceding compound were dissolved in 100 ml of liquid ammonia. The solvent was allowed to evaporate for about 2 hours. The residue was dissolved in a minimum amount of acetone and poured into ice water containing sufficient hydrochloric acid to render the mixture slightly acidic. The dye was extracted with methylene chloride. The extracts were washed with water, dried and finally evaporated to dryness under reduced pressure. The crystals obtained after treatment with petroleum ether were filtered and finally dried under sulfuric vacuum.

Obtained: 4.31 g Yield: 85% Red crystals M.P.=190° C. (dec.)

EXAMPLE 8

Preparation of
1-Hydroxy-2-propyl-3-phenyl-4-[4(3-chloro-4-hydroxyphenylazo)benzenesulfonamido]-7-[(2,4-ditert-amyl)-phenoxyacetyl]naphthamide

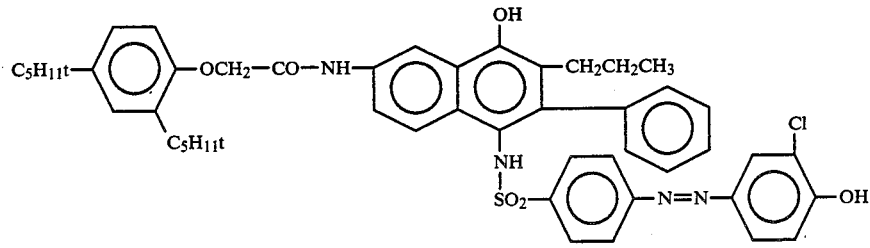

The three following solutions were left for 16 hours in contact under a nitrogen atmosphere.

3.21 g of 1-Hydroxy-2-propyl-3-phenyl-amino-7[(2,4-ditertamyl)phenoxyacetyl]naphthamide prepared in step (8) of Example 7, 2.12 g of (3-chloro-4-hydroxyphenylazo)-4-benzenesulfonyl chloride in 60 ml of methylene chloride, 0.45 g of pyridine in 11 ml of methylene chloride.

After reaction, the resulting solution was evaporated to dryness under reduced pressure. The crystals formed were washed with boiling "essence E", filtered, treated with petroleum ether and dried under a sulfuric vacuum. The crude material thus obtained was introduced little by little into 100 ml of liquid ammonia. After evaporation, the residue was dissolved in a minimum amount of acetone. The solution was poured into ice water containing hydrochloric acid. The precipitated dye was extracted with methylene chloride. The extracts were washed with water and dried before being submitted to evaporation under reduced pressure. The crystals obtained were washed with petroleum ether, drained and dried under a sulfuric vacuum.

Obtained: 3.1 g Yield: 63% Yellow crystals M.P.=130° C. (dec.)

EXAMPLE 9

A photographic element according to the invention was prepared which contained the magenta redox releaser compound prepared in example 1 and had the following structure (coverage ratios in mg/dm$^2$).

| Gelatin (5) | Hardener (0.16) |
|---|---|
| Ag$^+$ (5) | Magenta redox releaser compound of example 1 (8.4) |
|  | Gelatin (10.5) |

0.17 mm thick subbed poly(ethyleneterephthalate)-base

The light-sensitive emulsion was a green-sensitive silver halide negative emulsion and the hardener was bis-(vinylsulfonylmethyl)ether.

The photographic element was exposed in a sensitometer and developed with a viscous developer at a thickness of 0.14 mm at 20° C. while being laminated for 1 minute with a dye image receiving element.

The viscous developer comprised the following components:

Potassium hydroxide: 40 g
11-amino-undecanoic acid: 10 g
Oxalic acid: 5 g
Potassium bromide: 10 g
4-hydroxymethyl-4-methyl-1-phenyl-3-pyrazolidone: 1 g
Hydroxymethylcellulose: 35 g
Water to make 1 liter.

The pH was adjusted to 14.0 at 20° C.

The dye image receiving element comprised a paper base coated with a mordant layer which was a polymer corresponding to the following formula:

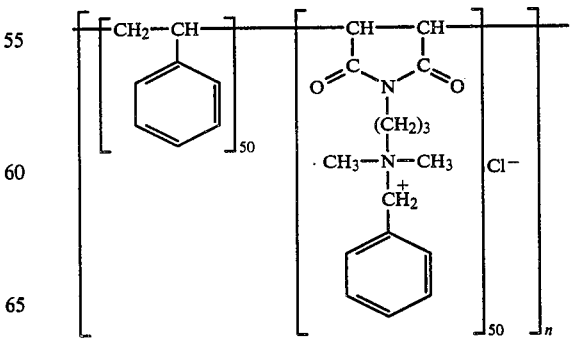

at a coverage of 21.5 mg/dm$^2$.

The above described procedure was repeated with development being prolonged for 2 min.

At the end of development, each processing sheet was peeled apart and processed in a tank with a bleach-fix solution having the following composition:
Monosodium salt of the ferric complex of ethylenediamine tetraacetic acid: 60 g
Neutral sodium sulfite: 12 g
Ammonium thiocyanate: 12 g
Ammonium thiosulfate: 120 g
Water to make 1 liter.

The pH was adjusted to 6.5 at 20° C.

The magenta redox releaser images retained in the photographic elements were then shifted by being treated in a tank for 5 seconds, in a 30 g/l potassium hydroxide solution.

The sensitometric characteristics of the retained magenta images and the developed silver coverage ratios are reported in table I.

TABLE I

| Development time (min) | SILVER IMAGE | | MAGENTA REDOX RELEASER IMAGE | | |
|---|---|---|---|---|---|
| | Maximum silver coverage (mg/dm$^2$) | Fog (mg/dm$^2$) | Dmax Green | Dmin Green | Dmin Blue |
| 1 | 1.19 | 0.04 | 1.56 | 0.49 | 0.25 |
| 2 | 1.41 | 0.10 | 0.94 | 0.18 | 0.13 |

EXAMPLE 10

A photographic element of the invention similar to the element of example 9 was prepared, but which contained the yellow redox releaser compound prepared in example 2 and had the following structure (coverage ratios in mg/dm$^2$)

| Gelatin (5) | Hardener (0.16) |
|---|---|
| Ag$^+$ (10) | Yellow redox releaser compound of example 2 (10.5) |
| | Gelatin (12.4) |
| 0.17 thick subbed poly(ethyleneterephthalate) base | |

This photographic product was exposed and processed as described in example 9 (development at pH=14).

The sensitometric results are given in table II.

TABLE II

| Development time (min) | SILVER IMAGE | | YELLOW REDOX RELEASER IMAGE | |
|---|---|---|---|---|
| | Maximum Ag coverage (mg/dm$^2$) | Fog (mg/dm$^2$) | Dmax Blue | Dmin Blue |
| 1 | 1.92 | 0.13 | 1.78 | 0.20 |
| 2 | 2.30 | 0.41 | 1.54 | 0.20 |
| 3 | 2.59 | 0.56 | 1.39 | 0.18 |

EXAMPLE 11

A photographic element of the invention was prepared, which contained the magenta redox releaser compound prepared in example 3 and had the following structure (coverage ratios in mg/dm$^2$).

| Gelatin (8) yellow colloidal silver (1) | Hardener (0.27) |
|---|---|
| Ag$^+$ (15) | Magenta redox releaser compound of example 3 (10) |

| Gelatin (8) yellow colloidal silver (1) | Hardener (0.27) |
|---|---|
| Gelatin (19) | |
| 0.17 mm subbed poly(ethyleneterephthalate) base | |

The silver halide light-sensitive emulsion and the hardener were such as described in example 9.

Two photographic controls (1) and (2) similar to those of the invention were prepared, except that the magenta redox releaser compound of example 2 was replaced by a magenta redox releaser compound of the prior art having the following formula:

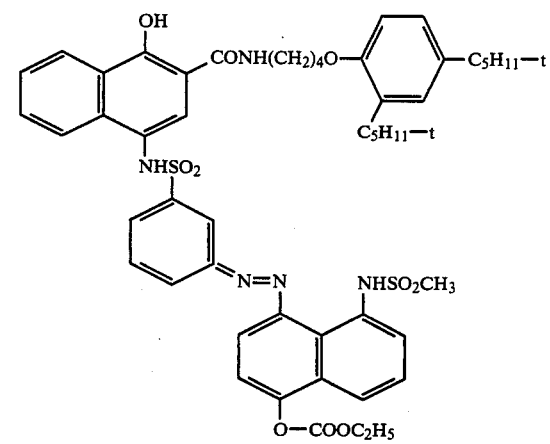

The control element (1) contained the non-purified redox releaser compound and the control element (2) contained the redox releaser compound purified by chromatography.

Both control elements and the element of the invention were exposed in a sensitometer and developed with a viscous developer laminated for 1 min at a thickness of 0.14 mm at 20° C. on a dye image receiving element such as described in example 9.

The viscous developer comprised the following components:
Potassium hydroxide: 40 g
11-amino-undecanoic acid: 20 g
KBr: 10 g
1-phenyl-4,4-dimethyl-3-pyrazolidone: 2 g
Hydroxymethylcellulose: 30 g
Water to make 1 liter At the end of the process step, the image receiving elements were peeled apart and the retained image elements were processed with the bleach-fix solution of example 9 for 2 min, and with the shifting solution for 5 sec.

The sensitometric results of the retained magenta image are gathered in table III.

TABLE III

| | Control element (1) | Control element (2) | Element of the invention |
|---|---|---|---|
| Dmax$^G$ | 1.92 | 1.56 | 1.03 |
| Dmax$^B$ | 0.64 | 0.62 | 0.36 |
| Dmin$_T{}^G$ | 0.11 | 0.10 | 0.14 |
| Dmin$_T{}^B$ | 0.14 | 0.11 | 0.06 |
| Stain | 0.09 | 0.06 | 0.01 |

EXAMPLE 12

A photographic element of the invention was prepared, containing the magenta redox releaser compound prepared in example 4 and having the following structure (coverage ratios in mg/dm²).

| Gelatin (5.5) | Hardener (0.14) |
|---|---|
| Ag⁺ (5) | Magenta redox releaser compound of example 4 (3) |
| | Gelatin (8.4) |
| 0.17 mm thick subbed poly(ethyleneterephthalate) base | |

The silver halide light-sensitive emulsion and the hardener were such as described in example 9.

In addition, two control photpgraphic elements (1) and (2) were prepared, which were similar to the element of the invention except that the magenta redox releaser compound of example 4 had been replaced, respectively by the prior art magenta redox releaser compounds that correspond to the following formulas:

Control magenta redox releaser

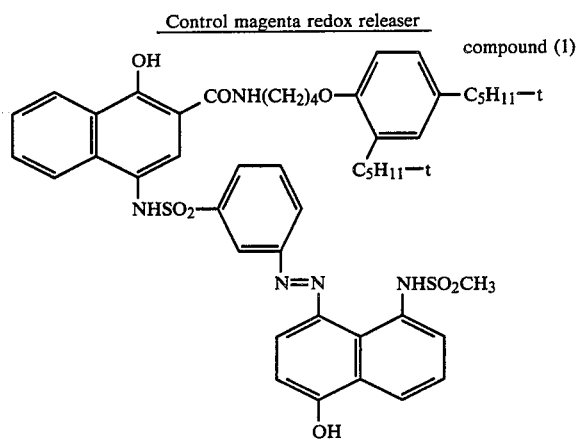

compound (1)

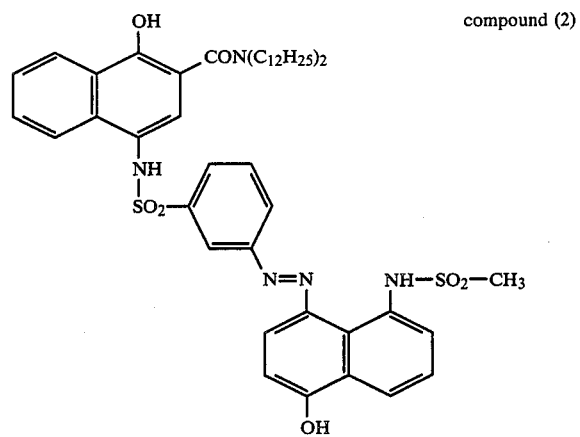

compound (2)

Control elements 1 and 2 had the following structures.

| Gelatin (5.5) | Hardener (0.14) |
|---|---|
| | Control element 1 |
| Ag⁺ (5) | Control magenta redox releaser compound (8) |
| | Gelatin (8) |
| | Control element 2 |
| Gelatin (5.5) | Hardener (0.14) |
| Ag⁺ (5) | Control magenta redox releaser compound 2 (8.4) |
| | Gelatin (8.4) |
| 0.17 mm thick subbed poly(ethyleneterephthalate) base | |

Both control photographic elements and the element of the invention were exposed in a sensitometer and developed as described in example 9, the development times being respectively 30 sec, 45 sec, 1 min, 1½ min. and 2 min.

At the end of the development step, the processing sheets were peeled apart and the photographic elements were processed with the bleach-fix solution described in example 9 for 2 min in a tank, followed by treatment with the shifting solution described in example 9.

The sensitometric results of the retained dye images are shown in tables IV, V, and VI.

TABLE IV

| | Control element (1) | | | |
|---|---|---|---|---|
| | Development time | | | |
| | 30 sec | 1 min | 1½ min | 2 min |
| D max$^G$ | 2.49 | 2.31 | 1.96 | 1.62 |
| D max$^B$ | 0.50 | 0.45 | 0.44 | 0.37 |
| D min$_T^G$ | 0.20 | 0.15 | 0.14 | 0.12 |
| D min$_T^B$ | 0.14 | 0.12 | 0.12 | 0.13 |
| Stain | 0.07 | 0.06 | 0.07 | 0.08 |

TABLE V

| | Control element (2) | | | | |
|---|---|---|---|---|---|
| | Development time | | | | |
| | 30 sec | 45 sec | 1 min | 1½ min | 2 min |
| Dmax$^G$ | 2.40 | 2.66 | 2.50 | 2.13 | 1.87 |
| Dmax$^B$ | 0.48 | 0.48 | 0.46 | 0.47 | 0.45 |
| Dmin$_T^G$ | 0.58 | 0.20 | 0.09 | 0.09 | 0.07 |
| Dmin$_T^B$ | 0.17 | 0.10 | 0.10 | 0.12 | 0.10 |
| Stain | 0.03 | 0.05 | 0.06 | 0.08 | 0.06 |

TABLE IV

| | Element of the invention | | | |
|---|---|---|---|---|
| | Development time | | | |
| | 30 sec | 1 min | 1½ min | 2 min |
| Dmax$^G$ | 0.79 | 0.71 | 0.68 | 0.49 |
| Dmax$^B$ | 0.19 | 0.16 | 0.15 | 0.14 |
| Dmin$_T^G$ | 0.07 | 0.06 | 0.08 | 0.08 |
| Dmin$_T^B$ | 0.05 | 0.05 | 0.07 | 0.08 |
| Stain | 0.01 | 0.01 | 0.09 | 0.04 |

The results of tables IV, V, and VI show that the photographic elements of the invention containing redox releaser compounds corresponding to the previously defined formula provide retained images exhibiting substantially reduced stain.

EXAMPLE 13

The procedure of example 12 was repeated, but the viscous developer was replaced, respectively, by one of the following developers A and B, used at 18° C. for 2 min.

| | Developer A | Developer B |
|---|---|---|
| 3-amino-propanol | 15 ml | 15 ml |
| SO₃Na₂ | 0 | 25 g |
| Benzyl alcohol | 10 ml | 10 ml |

-continued

|  | Developer A | Developer B |
|---|---|---|
| KBr | 3 g | 3 g |
| 1-phenyl-3-pyrazolidone | 0.5 g | 0.5 g |
| Hydroxyethylcellulose | 35 g | 35 g |
| Water to make 1 liter. | | |

The pH was adjusted to 11.5 with a solution of sodium hydroxide and of bis-sodium salt of phosphoric acid.

The sensitomeric results are reported in the following tables VII and VIII.

TABLE VII

| | Developer A | | |
|---|---|---|---|
| | Control element (1) | Control element (2) | Element of the invention |
| Max. Ag° coverage (mg/dm$^2$) | 2.9 | 2.0 | 1.0 |
| Silver fog (mg/dm$^2$) | 0.3 | 0.2 | 0.15 |
| Dmax$^G$ | 3.12 | 2.6 | 0.80 |
| Dmax$^B$ | 0.60 | 0.50 | 0.21 |
| Dmin$_T^G$ | 0.91 | 0.08 | 0.07 |
| Dmin$_T^B$ | 0.27 | 0.07 | 0.05 |
| Stain | 0.06 | 0.03 | 0.01 |

TABLE VIII

| | Developer B | | |
|---|---|---|---|
| | Control element (1) | Control element (2) | Element of the invention |
| Max. Ag° coverage (mg/dm$^2$) | 2.8 | 2.1 | 0.8 |
| Silver fog (mg/dm$^2$) | 0.45 | 0.3 | 0.1 |
| Dmax$^G$ | 2.87 | 2.60 | 0.73 |
| Dmax$^B$ | 0.56 | 0.56 | 0.21 |
| Dmin$_T^G$ | 0.18 | 0.12 | 0.13 |
| Dmin$_T^B$ | 0.10 | 0.08 | 0.06 |
| Stain | 0.04 | 0.03 | 0.01 |

The results of tables VII and VIII show that the photographic elements of the invention containing redox releaser compounds corresponding to the previously defined formula provide retained images exhibiting substantially reduced stain.

EXAMPLE 14

A photographic element according to the invention was prepared, which contained the magenta redox releaser compound prepared in example 5 and had the following structure (coverage ratio in mg/dm$^2$).

| Gelatin (8) | Hardener (0.20) |
|---|---|
| Ag$^+$ (11) | Magenta redox releaser compound of example 5 (4.85) |
| Developing agent (1.46) | Gelatin (13) |
| 0.17 mm thick subbed poly(ethyleneterephthalate) base | |

The silver halide light-sensitive emulsion and the hardener were such as described in example 9. The developing agent was the acetylated derivative of 1-phenyl-4,4-dimethyl-3-pyrazolidone.

In addition, a control photographic element was prepared which contained the magenta redox releaser compound corresponding to the following formula:

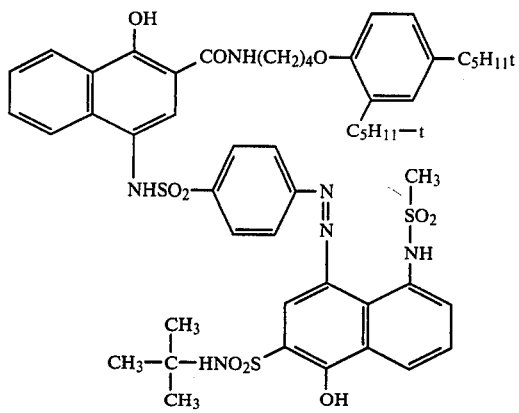

The structure of the control photographic element is given hereafter:

| Gelatin (12) | |
|---|---|
| Ag$^+$ (15) | Control magenta redox releaser compound (10) |
| Developing agent (2) Hardener (0.35) Gelatin (24) | |
| 0.17 mm thick subbed poly(ethyleneterephthalate) film support | |

Both photographic elements were exposed in a sensitometer and developed as described in example 9, but using development times respectively equal to 30 sec, 35 sec, 40 sec and 45 sec, and a viscous alkaline activator having the following composition:

Potassium hydroxide: 40 g
11-amino-undecanoic acid: 7.5 g
12-amino-dodecanoic acid: 2.5 g
Oxalic acid: 5 g
KBr: 10 g
Hydroxy-ethylcellulose: 30 g
Water to make 1 liter The photographic elements were processed with the bleach-fix solution described in example 9, and treated with a shifting solution consisting of the above activator and applied through an image receiving element, for 30 sec.

The sensitometric results are gathered in table IX.

TABLE XI

| | Control Element | Element of the invention | | | |
|---|---|---|---|---|---|
| | | Development time | | | |
| | 30 sec | 30 sec | 35 sec | 40 sec | 45 sec |
| Dmax$^G$ | 1.97 | 1.05 | 1.06 | 1.06 | 1.07 |
| Dmax$^B$ | 0.51 | 0.25 | 0.26 | 0.27 | 0.27 |
| Dmin$_T^G$ | 0.06 | 0.35 | 0.16 | 0.17 | 0.14 |
| Dmin$_T^B$ | 0.07 | 0.10 | 0.06 | 0.06 | 0.06 |
| Stain | 0.03 | 0.00 | 0.00 | 0.00 | 0.00 |

The results of table IX show the reduced stain of the photographic products of the invention that contain redox releaser colored compounds corresponding to the previously defined formula II.

EXAMPLE 15

The elimination of stain in the retained images formed in the photographic elements of the invention was also shown by repeating the procedure of example 14 with an alkaline activator which contained neither an amino acid nor oxalic acid.

The alkaline activator contained the following components:
Potassium hydroxide: 40 g
KBr: 10 g
Hydroxyethylcellulose: 40 g
Water to make 1 liter
Development was carried out at 18° C. for 50 s.
The sensitometric results are gathered in table X.

TABLE X

|  | Control Element | Element of the invention |
|---|---|---|
| $Dmax^G$ | 2.18 | 1.21 |
| $Dmax_B$ | 0.53 | 0.32 |
| $Dmin_T{}^G$ | 0.81 | 0.39 |
| $Dmin_T{}^B$ | 0.38 | 0.12 |
| Stain | 0.16 | 0.00 |

EXAMPLE 16

Four photographic elements according to the invention (1) (2) (3) and (4) containing respectively the following redox releaser compounds were prepared:
Element (1)—Redox releaser of example 6
Element (2)—Redox releaser J
Element (3)—Redox releaser K
Element (4)—Redox releaser M In addition five control photographic elements (I) (II) (III) (IV) and (V) were prepared which contained respectively redox releasers corresponding to the following formulas:

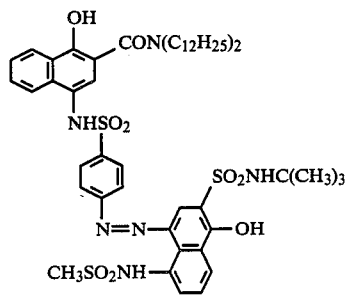  (I)

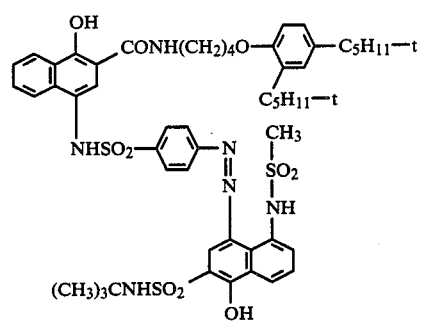  (II)

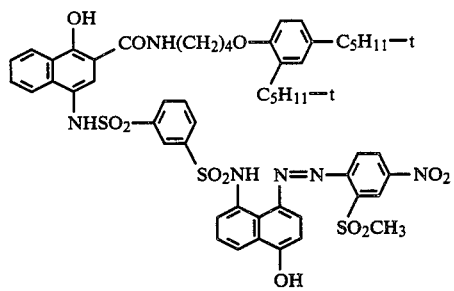  (III)

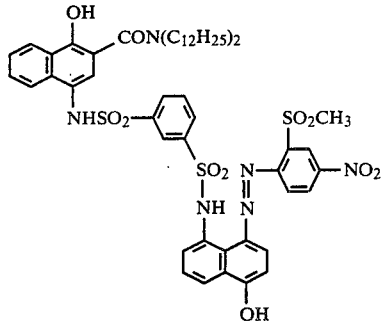  (IV)

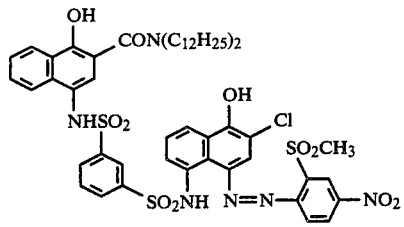  (V)

The structure of the photographic elements was the following (coverage ratios in mg/dm²).

| Gelatin (10.8) | |
|---|---|
| Ag⁺ (13.5) | Redox releaser compound (table XI hereafter) |
| | Gelatin (27) |
| | Subbed poly(ethyleneterephthalate) film support |

TABLE XI

| Photographic product | Redox releaser coverage (mg/dm²) |
|---|---|
| (1) | 14.6 |
| (2) | 13.5 |
| (3) | 9.7 |
| (4) | 9.7 |
| (I) | 12.9 |
| (II) | 10.8 |
| (III) | 8.6 |
| (IV) | 9.7 |
| (V) | 10.8 |

Four samples of each photographic element were exposed in a sensitometer and developed respectively in developers A and B defined hereafter at 38° C., for 1 min and 3 min.

| Developer A | |
|---|---|
| NaOH | 2.2 g |
| PO₄Na₃ | 38.8 g |
| SO₃Na₂ | 4.85 g |
| KBr | 10.0 g |
| 5-methylbenzotriazole | 0.1 g |
| 4-hydroxymethyl-4-methyl-1-phenyl-3-pyrazolidone | 0.3 g |
| 11-aminoundecanoic acid | 2.0 g |
| Water to make 1 liter | |
| The pH was adjusted to 11.5 | |
| Developer B | |
| NaOH | 20 g |
| KBr | 10 g |
| 5-methylbenzotriazole | 0.1 g |
| 4-hydroxymethyl-4-methyl-1-phenyl-3-pyrazolidone | 0.3 g |
| Water to make 1 liter | |
| The pH was adjusted to 13.7. | |

At the end of development, the photographic elements were washed, processed with a bleach-fix solution, washed and buffered at pH 7, at 38° C.

The coverages of developed Ag° and the sensitometric results are shown in table XII.

TABLE XII

| Photographic product | Developer and Development time (min) | Coverage Ag° L Emax (mg/dm$^2$) | Coverage Ag° Emin (mg/dm$^2$) | Green Dmax | Green Dmin | Blue Dmin |
|---|---|---|---|---|---|---|
| (I) (control) | B (1 min) | 3.1 | 0.21 | 3.36 | 0.18 | 0.18 |
| (I) | B (3 min) | 3.7 | 0.64 | 2.70 | 0.20 | 0.20 |
| (I) | A (1 min) | 2.5 | 0.21 | 3.50 | 0.24 | 0.18 |
| (I) | A (3 min) | 3.1 | 0.11 | 3.40 | 0.16 | 0.16 |
| (1) | B (1 min) | 2.9 | 0.11 | 3.38 | 0.18 | 0.12 |
| (1) | B (3 min) | 3.7 | 2.1 | 0.30 | 0.14 | 0.10 |
| (1) | A (1 min) | 2.7 | 0.11 | 3.50 | 0.12 | 0.10 |
| (1) | A (3 min) | 3.3 | 0.11 | 3.50 | 0.09 | 0.09 |
| (II) (control) | B (1 min) | — | — | 3.24 | 0.23 | 0.28 |
| (II) | B (3 min) | — | — | 2.20 | 0.20 | 0.28 |
| (II) | A (1 min) | — | — | 3.22 | 0.17 | 0.12 |
| (II) | A (3 min) | — | — | 3.12 | 0.16 | 0.12 |
| (2) | B (1 min) | 2.7 | 0.64 | 2.60 | 0.31 | 0.16 |
| (2) | B (3 min) | 4.3 | 2.6 | 0.30 | 0.26 | 0.16 |
| (2) | A (1 min) | 2.8 | 0.11 | 3.30 | 0.32 | 0.18 |
| (2) | A (3 min) | 2.6 | 0.11 | 3.30 | 0.26 | 0.17 |
| (III) (control) | B (1 min) | 3.5 | 0.11 | 3.60 | 0.38 | 0.22 |
| (III) | B (3 min) | 4.8 | 0.23 | 3.40 | 0.32 | 0.22 |
| (III) | A (1 min) | 3.6 | 0.11 | 3.64 | 0.32 | 0.12 |
| (III) | A (3 min) | 5.4 | 0.11 | 3.60 | 0.23 | 0.13 |
| (IV) (control) | B (1 min) | 2.8 | 0.11 | 3.16 | 0.16 | 0.14 |
| (IV) | B (3 min) | 3.7 | 0.23 | 2.52 | 0.14 | 0.14 |
| (IV) | A (1 min) | 1.3 | 0.11 | 3.06 | 0.41 | 0.12 |
| (IV) | A (3 min) | 2.3 | 0.11 | 3.20 | 0.22 | 0.11 |
| (3) | B (1 min) | 1.5 | 0.23 | 2.50 | 0.20 | 0.06 |
| (3) | B (3 min) | 2.7 | 0.53 | 1.09 | 0.13 | 0.06 |
| (3) | A (1 min) | 1.0 | 0.11 | 2.60 | 0.37 | 0.07 |
| (3) | A (3 min) | 1.8 | 0.11 | 2.53 | 0.14 | 0.06 |
| (V) (control) | B (1 min) | 2.4 | 0.11 | 2.80 | 0.12 | 0.14 |
| (V) | B (3 min) | — | — | 2.30 | 0.10 | 0.12 |
| (V) | A (1 min) | 1.2 | 0.11 | 2.94 | 0.76 | 0.12 |
| (V) | A (3 min) | 1.8 | 0.23 | 2.60 | 0.44 | 0.08 |
| (4) | B (1 min) | 1.6 | 0.11 | 3.06 | 0.64 | 0.12 |
| (4) | B (3 min) | 2.7 | 0.32 | 2.20 | .035 | 0.10 |
| (4) | A (1 min) | 1.2 | 0.11 | 3.10 | 0.98 | 0.13 |
| (4) | A (3 min) | 2.1 | 0.11 | 3.00 | 0.48 | 0.10 |

The results of table XII show that the photographic elements of the invention which contain redox releaser compounds corresponding to the previously defined general formula produce retained dye images having substantially improved blue $D_{min}$'s.

EXAMPLE 17

A photographic element of the invention was prepared containing the magenta redox releaser prepared in example 7 and having the following structure (coverage ratios in mg/dm$^2$).

| Gelatin (5.5) | Hardener (0.23) |
|---|---|
| Ag$^+$ (10) | Magenta redox releaser of example 7 (9) Gelatin (11.1) |

In addition, a photographic element of the invention was prepared containing the yellow redox releaser prepared in example 8 and having the following structure (coverage ratios in mg/dm$^2$).

| Gelatin (5.5) | Hardener (0.16) |
|---|---|
| Ag$^+$ (5) | Yellow redox releaser of example 8 (11) Gelatin (11) |

Both photographic elements were exposed in a sensitometer and developed with the viscous developer described in example 9. The element containing the magenta redox releaser was developed for 1½ min, and the element containing the yellow redox releaser was developed for 1 min.

At the end of development, the photographic elements were processed for 2 min with a bleach-fix solution, followed by a 5 sec bath in a shifting solution comprising 40 g/l potassium hydroxide in water.

The sensitometric characteristics of the retailed images are shown in Table XIII.

TABLE XIII

| | Blue | Green | Red |
|---|---|---|---|
| A. Magenta redox releaser (½ min development) | | | |
| Dmin | 0.16 | 0.14 | 0.04 |
| Dmax | 0.45 | 2.15 | 0.15 |
| B. Yellow redox releaser (1 min development) | | | |
| Dmin | 0.10 | | |
| Dmax | 1.20 | | |

The invention has been described in detail with particular reference to preferred embodiments thereof, but it will be understood that variations and modifications can be effected within the spirit and scope of the invention.

What is claimed is:

1. A nondiffusible sulfonamidonaphthol compound which is alkali-cleavable upon oxidation to release a diffusible photographically useful material, said nondiffusible sulfonamidonaphthol compound having the formula:

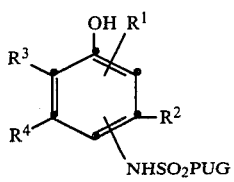

wherein:
(a) $R^1$ is alkyl, aryl, sulfamyl, carbamyl, carbonamido, carbonyl, carbonyloxy or sulfonamido;
(b) $R^2$ is alkyl having from 1 to 18 carbon atoms, aryl, or alkylphenyl having from 7 to 12 carbon atoms;
(c) $R^3$ and $R^4$, taken together with the phenol group, form a fused substituted naphthol group;
(d) PUG represents a photographically useful group; and
(e) at least one of $R^1$, $R^2$, $R^3$ or $R^4$, or any combination thereof, provides a molecular configuration of such size or shape as to render the compound non-diffusible under alkaline processing conditions.

2. The compound of claim 1 wherein PUG represents a dye or a dye precursor.

3. The compound of claim 1 wherein $R^1$ occupies the 2-position, $R^2$ occupies the 3-position, and $NHSO_2PUG$ occupies the 4-position of said sulfonamido compound.

4. The compound of claim 1 wherein $R^2$ represents an alkyl group having from 1 to 6 carbon atoms, or a phenyl group.

5. The compound of claim 1 wherein said compound is selected from the group consisting of the following compounds:
(a) 3,4,6-trimethyl-5-[3-(1-hydroxy-5-methanesulfonamido-4-naphthylazo)-benzenesulfonamido]-N,N-didodecylsalicylamide,
(b) 3,4,6-trimethyl-5-[4-(4-hydroxy-3-chlorophenylazo)-benzenesulfonamido]-N,N-didodecylsalicylamide,
(c) 1-hydroxy-3-methyl-4-[3-(1-carbethoxyoxy-5-methanesulfonamido-4-naphthylazo)phenylsulfonamido]-N-[4-(2,4-di-tert-amylphenoxy)butyl]-2-naphthamide,
(d) 1-hydroxy-3-methyl-4-[3-(1-hydroxy-5-methanesulfonamido-4-naphthylazo)phenylsulfonamido]-N-didodecyl-2-naphthamide,
(e) 1-hydroxy-3-methyl-4-[4-(1-hydroxy-2-(N-tert-butylsulfamoyl)-5-methanesulfonamido-4-naphthylazo)phenylsulfonamido]-4-[4-(2,4-di-tert-amylphenoxy)butyl]-2-naphthamide,
(f) 1-hydroxy-3-phenyl-4-[4-(1-hydroxy-2-N-tert-butylsulfamoyl-5-methanesulfonamido-4-naphthylazo)-phenylsulfonamido]-N-didodecyl-2-naphthamide, and
(g) 1-hydroxy-2-propyl-3-phenyl-4-[4(3-chloro-4-hydroxyphenylazo)benzenesulfonamido]-7-[2,4-di-tert-amylphenoxyacetyl]naphthamide.

* * * * *

UNITED STATES PATENT AND TRADEMARK OFFICE
CERTIFICATE OF CORRECTION

PATENT NO. : 4,605,697
DATED : August 12, 1986
INVENTOR(S) : C. F. Gerbal et al.

It is certified that error appears in the above-identified patent and that said Letters Patent are hereby corrected as shown below:

The title should read "SUBSTITUTED SULFONAMIDONAPHTHOL COMPOUNDS"

Column 52, claim 5, lines 7-12 should be deleted;

line 13, "(c)" should read --(a)--;

line 17, "(d)" should read --(b)--;

line 20, "(e)" should read --(c)--;

line 24, "(f)" should read --(d)--; and line 28, "(g)" should read --(e)--.

Signed and Sealed this

Twenty-sixth Day of January, 1988

Attest:

DONALD J. QUIGG

Attesting Officer      Commissioner of Patents and Trademarks